United States Patent [19]

Günter

[11] Patent Number: 5,361,762
[45] Date of Patent: Nov. 8, 1994

[54] APPARATUS FOR DETECTING PROPERTIES, DIFFERENCES AND CHANGES OF HUMAN OR ANIMAL BODIES

[75] Inventor: Kirchhoff Günter, Dachau, Germany

[73] Assignee: Handelsgesellschaft fur Medizin und Technik mit beschrankter Haftung, Dachau, Germany

[21] Appl. No.: 132,154

[22] Filed: Oct. 4, 1993

Related U.S. Application Data

[63] Continuation of Ser. No. 872,008, Apr. 22, 1992, abandoned, which is a continuation of Ser. No. 215,398, Jul. 5, 1988, Pat. No. 5,109,855.

[30] Foreign Application Priority Data

Jul. 6, 1987 [DE] Germany .................. 304671

[51] Int. Cl.$^5$ .............................. A61B 5/00
[52] U.S. Cl. .................. 128/653.1; 128/734
[58] Field of Search ............ 128/653.1, 735, 804, 128/907, 734

[56] References Cited

U.S. PATENT DOCUMENTS

2,930,977  3/1960  Machts .
4,135,131  1/1979  Larsen et al. .
4,240,445  12/1980  Iskander et al. .
4,848,357  7/1989  Wong et al. .
4,940,058  7/1990  Taff et al. .................. 128/653.1

FOREIGN PATENT DOCUMENTS

3430625  2/1986  Germany .
8520235  4/1986  Germany .
2137756  10/1984  United Kingdom .

*Primary Examiner*—Ruth S. Smith
*Attorney, Agent, or Firm*—Keck, Mahin & Cate

[57] ABSTRACT

An apparatus for detecting properties, differences and changes in human and animal bodies, using an a.c. source, which has one terminal that is directly or indirectly connected to the body to be examined, and an electric measuring device, which is coupled between the other terminal of the a.c. source and a sensing electrode. The sensing electrode is moved over the surface of the body and at least one spacer is provided on the sensing electrode so that the sensing electrode is spaced from the body. The electrode and the spacer are provided with at least one grounded layer, covering or shield consisting of conductive material. At least one of the layers, coverings or shields serves to shield the electrode and/or the lead connected to the electrode. The at least one grounded layer surrounding the sensing electrode consists of a conductive material serving to shield the sensing electrode and has a shield having a forward edge adapted to contact the body to be examined and to effect a grounding of the a.c. source.

3 Claims, 18 Drawing Sheets

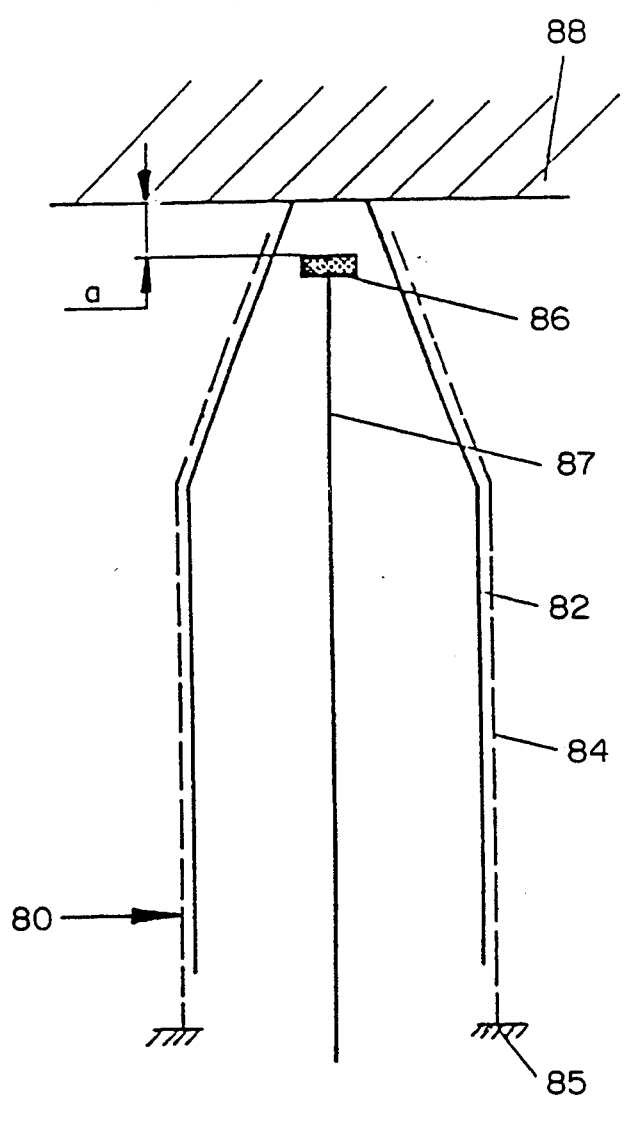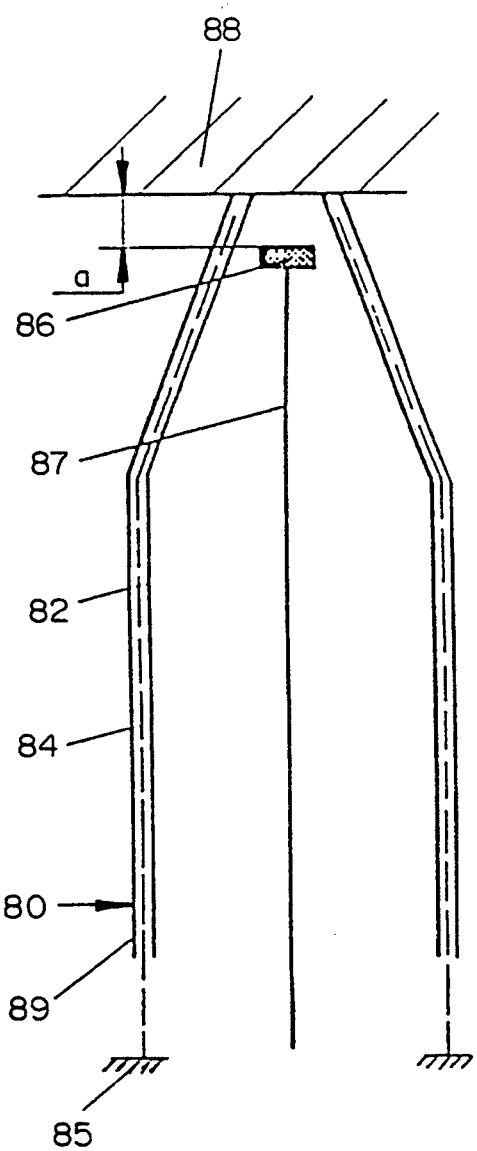

APPARATUS FOR DETECTING PROPERTIES, DIFFERENCES AND CHANGES OF HUMAN OR ANIMAL BODIES

This application is a continuation of U.S. patent application Ser. No. 07/872,008, filed Apr. 22, 1992, now abandoned which is a continuation of U.S. patent application Ser. No. 07/215,398, filed Jul. 5, 1988, now U.S. Pat. No. 5,109,855.

BACKGROUND OF THE INVENTION

1. Field of the Invention

This invention relates to an apparatus for detecting inhomogeneities in living or dead, human and animal bodies by means of radio-frequency electric voltages and currents of small magnitude. The measured variable is the strength of the electromagnetic field which is established by the radio-frequency electric energy in relation to a reference point (calibrated point) on a measuring member. A relative value is thus measured. At each point on the surface of the body, the field energy has a magnitude which will depend on the route along which the radio-frequency field has traveled in the body and on the conductances/impedances of the media/inhomogeneities that had to be traversed by that field.

One terminal of an alternating current source is directly connected to the body to be examined or is indirectly connected to it by capacitive means and causes said body to radiate like an antenna.

This measuring apparatus comprises a receiving electrode, which is moved towards the surface of the body at the locations where the measurements are to be made, and which measures the strength of the field which is emitted by the body. The two parts of the apparatus consisting of the transmitter and the receiver may be physically separate from each other so that certain advantages will be afforded in the manipulation of the apparatus, e.g., cables can substantially be avoided.

To measure the field strength of the tested body, the receiving electrode (probe electrode) is arranged at a distance from the surface of the body on which a measurement is to be taken at certain locations.

The apparatuses used for such a measuring method must be so designed that the radio-frequency electric energy which is employed will not result in damage to the human body or elsewhere so that the measurement may be repeated, preferably several times and, e.g., the progress or healing of a disease can be followed by means of the measured data and conclusions can be drawn therefrom. Disadvantages of other diagnostic processes, such as X-ray diagnosis, are to be avoided.

The avoiding of damage will also depend on the selection of suitable values for the frequency, voltage and current. An exciting frequency which is near natural frequencies of the body will result in an absorption and will cause the electrically excitable particles to perform natural vibrations. Such vibrations are used, e.g., in microwave therapy equipment for a generation of heat for therapeutic purposes in the tissue. In the use of such apparatus the power which is supplied must carefully be controlled, e.g., in order to prevent burns in the tissue.

The known X-rays, which can destroy cells, have frequencies in a range which is higher than that of a microwave apparatus.

The operating frequency which is used in the above-mentioned radio-frequency diagnosis method lies in a pass band of the cells and cell membranes so that the characteristic impedance has a real value. In the stop bands above and below the pass band the characteristic impedance becomes imaginary and an absorption is effected so that imaginary facts undesirably enter the result of the measurement. In experiments conducted in human bodies for decades it has been found that the frequency limits for useful operation are at 150 kHz on one side and 950 kHz on the other side.

2. Description of the Prior Art

Useful methods or designs are not known in the field of radio-frequency diagnosis. A method having numerous disadvantages has been described in German Patent Specification 950,402, the corresponding laid-open German Patent Application M 7 697 VIII d/30a (and the corresponding French Patent Specification 1,153,724, British Patent Specification 842,863, Swiss Patent Specification 352,781 and U.S. Pat. No. 2,930,977). Reference is also made to G. Bittner, "Über ein neues Verfahren der Elektrodiagnostik" in Electromedizin, 6 (1961), 3, pages 125 to 129, where the method discussed in the above-mentioned patent specifications has been described. In a booklet "Physikalische Grundlagen der Antroposkopie, Vorabdruck-auszugsweise-aus Propädeutik der Hochfrequenz-Diagnostik Band I: Wissenschaftliche Grundlagen", issued by Deutsche Gesellschaft für Hochfrequenz-Diagnostik e.V.-Anthroposkopie-Munich 1986, Paul A. Bross has explained the measuring method in detail. The medical fundamentals have been set forth briefly by R. Kirchhoff in "Physiologische und zytologische Grundlagen für die Anthroposkopie" in Erfahrungsheilkunde-Zeitschrift für die ärztliche Praxis-acta medica empirica, 29 (1980), 8, pages 662 to 664.

Only some important disadvantages of the numerous disadvantages of the known designs will now be set forth:

Under different contact pressures and in different positions of the measuring apparatus (e.g., inclinations) relative to the surface, different values were measured at the same measuring location.

In lines 20 et seq. on page 5, German Patent Specification 950,402 describes a probe having "a contact surface which consists of a material which will not influence the measurement. But such probe cannot be provided in practice because such a material cannot be conceived as every material has a certain specific relative dielectric constant which influences the conductivity for radio-frequency currents. Only air could be used as "material" having no influence on the measurement because air is also the "material" which surrounds the probe.

That example has been referred to only to facilitate the understanding of the fact that said known method cannot be used in practice if objective data are to be acquired.

Insufficient attention has been directed to the selection of the materials used to make the measuring electrode and, in particular, the significance of the relative dielectric constant of the material for a measurement at a radio frequency has not sufficiently been taken into account so that the results of the measurements taken in the practical use of the apparatuses were not reproducible.

Many of the apparatuses still embodied tube technology and for this reason did not permit some advantages of the measuring method to be achieved.

A further disadvantage resided in the fact that the measurements did not permit an adequate variation because it was difficult or impossible to detect and to correctly interpret inhomogeneities (such as foci of inflammations, on the one hand, or sclerosed tumors, on the other hand) in different depths.

German Utility Model Specification 85 20 235 describes an apparatus for detecting properties, differences and changes of the human living or dead body, comprising an a.c. source, which has one terminal that is directly connected to the body to be examined, and an electric measuring device, which is coupled between the other terminal of the a.c. source and a sensing electrode, which is moved over the surface of the body, wherein spacers are provided on the sensing electrode and the sensing electrode is spaced from that surface of the apparatus which is moved in contact with the body. Within a housing that known apparatus may comprise a shield for preventing disturbing influences to be exerted on an electrode which is spaced from the surface of a body. But that shield must necessarily be disposed within the housing and cannot be removed from that housing. For this reason it is difficult to effect a leakage by a contact with those edges of the shield which face the body, i.e., the tip of the sensing device, so that it is still impossible automatically to detect signals and the correct approach of the apparatus to the body is a difficult operation because it will depend on a visual estimate. Besides, the apparatus cannot be designed to have a high sensitivity and to create a sufficiently small interference at the same time.

U.S. Pat. No. 4,240,445 (see particularly its FIGS. 2 and 3), discloses an apparatus which is of the kind described first hereinbefore and which is provided on its housing with a low superstructure including a strip conductor (electrode) and lateral shields, which surround said strip conductor and are soldered to a shield which also surrounds the strip conductor but is disposed within the housing. An insulating cover layer is also provided. The lateral shields are not provided directly on the housing and do not have a forward edge so that known device does not permit a leakage of the radio-frequency field by a contact with the body to be measured. Besides, the effect of the shield cannot be changed by a variation of the contact pressure between that apparatus and the skin with the result that said effect will be reduced in case of a low contact pressure and will be increased under a higher contact pressure.

German Patent Publication 1,126,559 discloses an apparatus for measuring pulse-synchronized capacitive impedance changes which depend on the blood flow in cell tissues in the depth of hollow organs of human beings or animals, such as the skull, the eye or similar parts of the body. That apparatus comprises electrodes which are connected to a source of radio-frequency energy and uses the pulse-synchronized change of the biological dielectric as a partial capacitance of a radio-frequency resonant circuit in order to modulate the frequency of that circuit. That device comprises sensing electrodes, which have a small surface, and a preferably non-conductive body, particularly a body having an extremely high dielectric constant, is disposed between said electrodes and the object in a manner known per se. That body is surrounded by a covering, which is made of elastic material having a very low dielectric constant. The body and the covering are so designed that they can jointly be forced under a variable pressure against the surface of the object in a manner known per se and said contact pressure is so high that the sphygnoidal changes occurring in the bloodless cell tissue under the contact surface will be suppressed. A radio-frequency voltage is applied in a manner known per se to the electrodes for a determination of the sphygnoidal impedance changes of the dielectric disposed between the electrodes. The measuring circuit is preferably coupled to a resonant circuit of an oscillator to modulate the frequency thereof. But that printed publication relates only to a transmitter. Whereas that transmitter comprises an electrode and lateral shields surrounding said electrode, said electrode and shield are disposed inside a housing and there is no reference to a shield at all in connection with the receiving electrodes.

German Patent Specification 961,827 discloses an electrode array for therapeutic apparatus for the medical treatment effected in a capacitor field of short-wave or ultra-short-wave electric oscillations. In that array the electrode is disposed in a cap (electrode shoe) and is spaced from the surface to be treated, and a second distance can be adjusted in that an adapter (fore-shoe) is mounted in front of the cap. The shell of the cap is slightly tapered and the (bottomless) adapter has the same shape so that the adapter when mounted on the cap will be retained thereon by a wedgelike fit. That cap also constitutes only a transmitter and does not contain a conductive shield.

SUMMARY OF THE INVENTION

It is an object of the invention to avoid the disadvantages of the known apparatuses which have been discussed and to improve said apparatuses by the provision of an apparatus for detecting properties, differences and changes of human or animal living or dead bodies. The apparatus comprising an a.c. source, which has one terminal that is directly or indirectly connected to the body to be examined, and an electric measuring device, which is coupled between the other terminal of the a.c. source and a sensing electrode, which is moved over the surface of the body, wherein at least one spacer is provided on the sensing electrode and the sensing electrode is spaced from that surface of the apparatus which is moved in contact with the body. That apparatus should be adapted to be handled more conveniently and more reliably and should furnish substantially stable measured values and should be adaptable for an automatic recording and acquisition of the measured values.

The object set forth hereinbefore has surprisingly been accomplished by the invention. Independently of the improvements which have been enabled by the general progress of technological knowledge, the experiments which have been conducted in the laboratory and in the field for decades have resulted in some conspicuous improvements and particularly in the provision of various shields which produce interesting and unexpected results regarding a convenient use and the acquisition of reproducible measured values.

The invention provides an apparatus for detecting properties, differences and changes of human or animal living or dead bodies, comprising an a.c. source, which has one terminal that is directly or indirectly connected to the body to be examined, and an electric measuring device, which is coupled between the other terminal of the a.c. source and a sensing electrode, which is moved over the surface of the body, wherein at least one spacer is provided on the sensing electrode and the sensing electrode is spaced from that surface of the apparatus which is moved in contact with the body, wherein the electrode and/or the spacer and/or any housing which is provided is provided with at least one grounded layer, covering or shield consisting of conductive material or conductive paint, and, if a housing is provided, at least one of said layers, coverings or shields is disposed entirely or in part on the outside of the housing or within the wall of the housing, and said at least one layer, covering or shield serves to shield the electrode and/or the lead connected to said electrode. That apparatus is characterized in that the shield, which is optionally provided entirely or in part with an insulation, comprises a forward edge, which is adapted to contact the body to be examined and to effect a leakage of the radio-frequency field. In that statement the term "provided" means that the electrode is not connected to the at least one shield by conductive means.

The sensing apparatuses in accordance with the invention are usually cylindrical but may alternatively have different shapes and may, for instance, be spherical or prismatic.

The sensing body is that part of the receiver part of the apparatus in accordance with the invention which should be contacted with or impressed into the human or animal body that is to be examined. In most cases the sensing body consists of a housing although embodiments having no housing may be conceived.

The shield which is connected to ground or to a low electric potential which effects a shielding or leakage like the ground potential will change the influence of the radiation from the antenna on the electrode. That is essential for a convenient handling of the measuring set-up and for a measurement of sufficiently stable values.

In the use of the apparatus in accordance with the invention a response of the body, e.g., a generation of heat, will be avoided. Otherwise the values which are measured would not reflect the instantaneous condition of unbiased tissues and organs but a state which has been changed by responses.

Owing to the provision of at least one shield on the outside of the housing and/or within the wall of the housing, which wall is arranged to contact the body to be measured and to effect a leakage of the radio-frequency field, the following advantages are afforded:

a) Owing to the provision of shields on the outside of the housing, those edges of the shield which face the body, i.e., the sensing tip, can be used to effect a leakage. This can be achieved only with difficulties with internally disposed shield. Such shields may be used, e.g., for an automatic detection of signals (peak values measured) or for an indication of the angle at which the sensing body is applied because a correct result of the measurement will not be obtained unless the sensing body is applied to the surface at right angles thereto.

b) If the sensing body is to be as thin as possible for an introduction into the throat cavity or into other cavities which are open or have been opened toward the outside, such as the vagina, care must be taken that the shield is not very close to the electrode and to the conducting means leading from the electrode to the measuring device because otherwise the resulting capacity will too strongly attenuate the signals being received. An external shield will be more favorable than an internal shield because the former is spaced a larger distance apart from the electrode.

c) In some territories, very strict regulations are in force for the operation of radio-frequency transmitters so that only extremely low powers are permitted for the operation of transmitters at suitable frequencies. For this reason a high capacitance resulting in the reception of a strong signal must be provided to ensure that the receiver will have the highest possible sensitivity whereas the transmitter power will be minimized so that it will not exceed the permissible value. If the shield is sufficiently spaced from the receiving electrode and from the conductive material connected to said electrode, e.g., a lead wire, that requirement will be met and the transmitter powers which are required will be minimized.

d) A change of the effect of the shield will be of advantage in some embodiments. In some embodiments, external shields can desirably be displaced toward or away from the sensing tip.

In the efforts to accomplish the object set forth it has been recognized that numerous advantages, even advantages which had not been hoped for at the beginning, can be afforded by the provision of differently designed and differently acting shields associated with the electrodes of the sensing bodies. For instance, the susceptibility to interference can be decreased to a negligible value and the measurement can be automated if specially shaped and specially shielded measuring electrodes are used. Because each electrode-shield combination has a characteristic of its own, a set of sensing bodies can be provided which are capable of an optimum adjustment in adaptation to specific portions of the body.

Important advantages have been afforded by the selection of the shape and material of the dielectric that is disposed between the sensing electrode and the location at which the body is sensed. In that context any dielectric, regardless of its state of matter, can be used for that purpose. Besides, the experiments have shown that a selective change of the shape and material of the electrode, and of the associated shield and the spacing of the electrode may be required for a fast and improved differentiation of measured values which suggest the presence of inhomogeneities because with respect to a given location of measurement a change in form, material, spacing and shield will result in different measured values so that conclusions will be possible regarding certain properties of the processes which result in the inhomogeneity.

The legal provisions relating to the operation of radio-frequency equipment are different in different countries. Specifically, different limits have been or will be legally prescribed regarding the permissible value of the interference field variable. If radio-frequency apparatuses of the kind concerned are to be operated everywhere without a need for special precautions, standard equipment must be used for the transmitter power and modulation and the sensitivity of the receiver which is incorporated in the apparatus. But the use of such standard equipment will not make sense unless the actual sensitivity on the receiving side can be varied by means of receiving electrodes (sensing electrodes) which differ in size and the transmitter power is then increased until the highest permissible interference level has been reached; such an increase of power will result in considerable advantages regarding the measurement, in some cases. That practice may be adopted with the apparatus in accordance with the invention comprising a sensing body provided with shielded electrodes having widely variable characteristics.

For measuring apparatus for medical use, optimum safety is required for patients and operators. For this purpose the possibility of a radio-frequency diagnosis which will give stable measured values in spite of the use of harmless frequencies and low voltages is a particularly great advantage.

For the practical handling of the apparatus it was also necessary to provide a stationary apparatus for use in a medical office and a portable unit for use during home visits. Owing to the above-mentioned criteria which are met by the electrodes, the power supply and the use of corresponding identical components, the results of measurements carried out with measuring apparatuses of the two different types on the same body to be examined were perfectly identical.

This has also been due to the fact that the receiving electrode is calibrated to eliminate all influences which are not related to the location of the measurement on the human or animal patient. Attention is directed to the above-mentioned publication by Bross, particularly to his description of the "passive electrical four-terminal network", which ensures that the measured value will be influenced only by those field changes which are detected at the variable fourth terminal, i.e., at said location.

In the apparatus in accordance with the invention the transmitting section preferably transmits a radio-frequency oscillation which is unaffected by the shield and is at a frequency in the range from 150 to 950 kHz. Frequencies in the range from 250 to 700 kHz are particularly preferred.

The frequencies used for the present radio-frequency diagnosis preferably lie between the two frequencies of 150 kHz and 950 kHz which are known for human beings. An almost complete transmission and an absence of attenuation can be achieved in that range. This means that responses of the body being examined will virtually be avoided in the measuring method performed with the apparatus in accordance with the invention and there will be no polarity reversal or changes of the skin resistance at the acupuncture or neural points. As a result, the measured values will remain stable when the electrode is closely applied; this cannot be achieved in different methods and with known apparatuses.

If a spontaneous leakage by a contact with the forward edge of the shield is desired, any insulation provided at the shield will be relatively thin and/or will be made of a material having a relatively high dielectric constant. If such a spontaneous leakage is not desired, the insulation will be relatively thick and/or made of a material having a relatively low dielectric constant.

In a suitable embodiment of the invention, the shield or at least one of the shields protrudes from the housing and is movable into the housing.

In another suitable embodiment of the invention at least one shield is not connected to ground but is connected to a low electric potential, which effects a shielding or leakage like a ground potential.

In another suitable embodiment of the apparatus in accordance with the invention there is a clearance between the electrode and the end of the housing.

In another suitable embodiment of the apparatus in accordance with the invention the spacer consists of deformable material.

In another suitable embodiment of the invention the at least one spacer and optionally also the shield is detachably provided on the housing.

In a particularly desirable embodiment of the apparatus in accordance with the invention the at least one spacer and the shield consist of different materials having different dielectric constants.

In a further particularly desirable embodiment of the apparatus in accordance with the invention, a selective change of the effect of the shield is permitted in that a plurality of spacers are arranged one over the other and said spacers are optionally interchangeable or can be altered in number.

In a still more desirable embodiment of the apparatus in accordance with the invention the position of the at least one shielding spacer and/or the shielding part of the housing relative to the electrode is variable.

In another suitable embodiment of the apparatus in accordance with the invention the shield associated with the electrode is provided on the housing to be detachable from the housing together with or without the electrode.

In the apparatus in accordance with the invention the entire shield or part of the shield may be provided on one or more spherical or disk-shaped spacers and/or housing parts provided with a handle.

In an even more preferred embodiment of the apparatus in accordance with the invention the shield is conductively connected to ground or to a low electric potential which effects a shielding or leakage like a ground potential, the shield is provided on the outside of the housing for the electrode and the thickness, the density and/or the extent of the shield extending toward the tip of the housing or to the electrode or to the at least one spacer are different. It is emphasized that concept can be adopted also in the other embodiments with other or more specific design features.

In a special embodiment of the apparatus in accordance with the invention, certain important advantages are afforded owing to the shape, the selected materials, the distance between the electrode and sensing tip and the special nature and design of the shielding means (grounding means): Whereas theoretical considerations and calculations had no chance of success, practical experiments have shown that when a depression is formed in the surface of the body under the pressure applied, the bulging of the tissue under the pressure applied and the resulting higher local field strength will be compensated for by the additionally acting shield in such a manner that the measured value will remain the same. In that embodiment the measured value will not depend on the pressure applied (which may be measured in grams) but on the effect of that pressure, which may be equal in magnitude even with tissues which differ in compliance. As a result, reproducible measured values will be obtained with that embodiment. That fact is taken into account in a particularly desirable embodiment of the apparatus in accordance with the invention, in which the material and/or the size or shape of the at least one spacer and/or the surrounding housing space and/or housing part are selected to match the material or the size or shape of the electrode in such a manner that the effect which is exerted on the electrode and/or the electrode lead by the intensity pattern of the radiated field which is due to the depression in the surface of the body being examined will be compensated for by the shield. In that embodiment the shield is suitably provided with an insulation which is relatively thick and/or consists of a material having a relatively low dielectric constant. The combined actions of the shield and of the radio-frequency radiation received by the electrode will be obtained, e.g., in that the metallic layer of the shield extending toward the tip of the sensing body is thinner and is optionally provided with holes, which increase in size toward the tip so that portion of the shield does not shield the electrode as strongly as that portion of the shield which is thicker or unapertured. On the other hand, an impression of the sensing body into the surface of the body to a larger depth will increase the strength of the radio-frequency radiation because the radiation will act also laterally. As the sensing body is impressed to a larger depth, the effect of the thicker shield will increase. On the other hand, if the sensing body is impressed to a smaller depth, the strength of the radio-frequency radiation will be decreased so that a smaller shielding action is required. This is achieved in that the shielding material is dimensioned as described hereinbefore. If the dimensions of the sensing body, the distance from the tip of said body to the electrode, the dimensions of the electrode and the dimensions of the shield are selected in consideration of the above-mentioned interrelations, the values can almost entirely be combined so that the measured value will remain the same during the measurement even in case of a very large variation of the pressure applied.

In general, the thickness and the material of the insulation provided on the shield will suitably be selected in dependence on the leakage which is to be effected by the contact with the forward edge of the shield. In the embodiment described in the preceding paragraph the insulation is desirably relatively thick and/or made of a material having a relatively low dielectric constant so that a spontaneous leakage by the contact with the forward edges of the shield will be prevented.

In a particularly preferred embodiment of the invention the housing of the sensing body is provided on the outside with a shielding ring, which is connected to ground or to a low electric potential which effects a shielding or leakage like a ground potential and said shielding ring is fixed or is adjustable in position.

The shielding ring is preferably connected to a metal layer which is provided on the outside of the housing of the sensing body or is connected by conductive fixing means or contacts to the shield which is disposed inside the housing of the sensing body.

In a particularly desirable embodiment of the apparatus according to the invention the shielding ring is replaceable by another shielding ring which has a smaller or larger outside surface or a smaller or larger rim.

In a particularly preferred embodiment of the apparatus in accordance with the invention the metallic or metallized boundary (edge) which is provided on the housing of the sensing body and serves for effecting a ground leakage can be varied in that it is designed to selectively receive insulating caps which differ in size so that the effective boundary (edge) can be displaced.

The apparatus according to the invention, comprising a sensing body having a special external shield, permits an automatic acquisition, processing and display of data. Because a leakage of the radio-frequency energy to ground or to a low electric potential which effects a shielding or leakage like a ground potential is effected at a time at which an impression in a predetermined depth has been formed on the surface of the body, the conditions of measurement will be identical at all locations at which measurements are taken. A repetition of the measurement at a given location will result in exactly the same value. It will be sufficient for the computer to record only the peak value for each measurement and, in case of a plurality of consecutive measurements at the same location, the computer may calculate the average of said peak values and may then automatically process said average in the usual manner. When the apparatus has previously been calibrated at a calibration point (reference point) of the body in the same mode of measurement, i.e., with an impression of the sensing member until a peak value has been recorded, the subsequent measurements always result in reproducible measured values although said values will differ in case of any inhomogeneities which are desired to be detected for a diagnosis. That automatic measurement will reliably avoid any error in the reading of an instrument and in manual writing of data.

In a particularly preferred embodiment of the apparatus in accordance with the invention the apparatus is adapted to be connected to an apparatus (computer) for a recording of measured data, which apparatus serves for a continual automatic acquisition of the data which are measured in dependence on the pressure applied and for a retrievable storage of those two peak values which have been obtained immediately before and immediately after the contact between the edges or the shielding rings and the body to be examined.

The mode of operation of that embodiment will now be described in more detail. The sensing body comprising the receiving electrode is applied by the operator under a progressively increasing pressure to the body at the location which is to be examined and the value which is received by the apparatus for recording measured data increases until the edges or rings of the shield have reached the body at the location to be examined after a peak value has been measured shortly before. At that time the measured value will drop suddenly and will remain low even when a higher pressure is applied. When the sensing body is then retracted to effect a pressure relief, the low values will be maintained until the edges or rings of the shield have cleared the body to be examined. At that time the apparatus for recording measured data will suddenly detect a peak value again. Only said two peak values will be retrievably stored by the apparatus for recording measured data and only the detection of these two peak values will permit the generation of a retrievable measured value, suitably as an average. If the operator fails to impress the sensing body to such a depth that the peak value is reached before the edges or rings of the shield contact the body at the location to be examined, so that a peak value is measured but is not correct, then a retrievable value will not be stored and the operator will know that he or she has not performed a correct operation. In a simplified mode, a single peak value may be sufficient if the operation is performed with adequate care.

The electrode may suitably be made of a deformable conductive material, which is adapted to increase or reduce its receiving surface for radio-frequency energy in response to pressure applied, and the shield may be provided on the inside with an insulating layer.

In another suitable embodiment of the apparatus in accordance with the invention the housing of the sensing body is provided on its forward side portion or at its tip with a snap fastener or with other fastening means for a detachable connection to mating fastening means provided on a preferably flexible surface, which may selectively have different sizes or shapes and which may or may not be provided with a shield.

In a further suitable embodiment of the apparatus in accordance with the invention the housing of the sensing body comprises a permanently or detachably mounted portion which is made of a deformable and preferably flexible material and which may or may not be provided with a shield and is adapted to adapt itself to the surface of the body to be examined.

In a particularly desirable embodiment of the apparatus in accordance with the invention the metallic shield which is disposed in the interior of the housing for the electrode consists of a tube, which is fixedly mounted or is displaceable along its longitudinal axis and which may be provided with apertures, which differ in size and shape and are differently distributed over the surface of the tube and serve to change the shielding action.

In another particularly desirable embodiment of the apparatus in accordance with the invention the forward portion of the housing of the sensing body is provided with an internally attached electrode, which is connectable to the measuring device by flexible means and which is mounted to be displaceable or screwable.

In another particularly desirable embodiment of the apparatus in accordance with the invention a sensing body which is usable in cavities of the body to be examined and which is provided with a shield is accommodated in a housing, which is pivoted on one or more axes and provided with leads which are pivoted on one or more axes. Such an apparatus will be particularly suitable for an examination of gingiva and other portions of the throat and also for an examination of the vagina.

In another particularly desirable embodiment of the apparatus in accordance with the invention a front portion of the housing of the sensing body consists of an adjusting screw which can be screwed in and out to change the distance between the electrode and the surface to be measured and for a change of the effect of the shield.

In a preferred arrangement, the adjusting screw comprises a deformable lower portion, which ensures that the space which is formed during an unscrewing of the adjusting screw will be filled with an elastically deformable material, which will be compressed as the adjusting screw is screwed in.

An additional diagnosis is permitted by the above-mentioned special features relating to the selection of the frequency, voltage, current value and of the dimensions of the shielded sensing body that is incorporated in the apparatus in accordance with the invention and is to be applied to the patient:

In the use of the known measuring devices in conjunction with acupuncture it is very difficult to measure a stable value at the acupuncture or neural points. On the other hand, the acupuncture and neural points can perfectly be detected by means of the apparatus in accordance with the invention if the sensing body comprises a metallic tip or a metallic pin which is very closely spaced from the skin.

A small distance from the skin can be ensured, e.g., by the provision of a simple thin coat of paint or another insulating material. A shielding of the electrode will also have the desirable result that the result of the measurement will not be affected by lateral influences. The shield is provided on its inside surface facing the electrode with an insulating layer and may be provided with an insulating coating also on the outside. The sensing body may be provided at its tip with an edge for marking the location which has been detected on the body, e.g., an acupuncture point, so that that point can be subjected to therapy immediately thereafter, e.g., by means of a needle.

For this reason, in a particularly preferred embodiment of the apparatus in accordance with the invention the spacer associated with the electrode consists only of a coat of paint or another thin insulating covering, which may be provided with a more or less extensive shield, which may extend over the electrode, which is also painted or provided with another thin insulating covering.

In another suitable embodiment of the apparatus in accordance with the invention the insulated electrode is formed at its forward tip with an edge, which may have any desired shape and serves to conveniently mark a significant location which has been detected on the skin.

The apparatus in accordance with the invention permits a reliable and unbiased search for certain points. This is significant also for the non-medical handling of the apparatus in the so-called autotherapy because a fast analgetic therapy which is effective for a reasonable time can quickly be effected at certain known acupuncture and neural points. If only that use by private persons is desired, the transmitting and receiving sections of the apparatus may be simplified in that much lower voltages may be used and the apparatus may be provided with a very small housing to which the sensing tip is attached. No cables will be required in that case because the required contact will be established in a circuit which comprises the contact of the hand with the apparatus at a metal contact plate or, in case of a treatment of a patient by another person, by a contact between the patient and such other person.

In a suitable embodiment of the apparatus in accordance with the invention the transmitting and receiving sections as well as the power supply are accommodated in a common housing, there are no connecting cables from the transmitting section to the body to be examined and from the receiving section to the sensing body, and the apparatus is provided with a contacting metal part for making the required electric contact to the transmitter by manual touch so that the transmitted energy will be conducted through the body to be examined and optionally through the interposed body of the treating person. If that embodiment is used for a treatment of a patient by another person, the energy will be transmitted by the contact of the hand of the treating person with the body to be examined, and in case of autotherapy a treating person will not be included in the circuit but the person who effects autotherapy will contact the contact part so that the transmitted energy will directly be conducted by him or her.

The desire to simplify technical structures and, e.g., to eliminate cables or at least to reduce them in length is obvious and as such need not be mentioned. But in the apparatus in accordance with the invention any shielded radio-frequency cables (coaxial cables) would constitute a source of errors because the extremely low voltages and currents employed may change in response to even very small changes in capacitance. For instance, a flexing of the cable may result in a change of the capacitance between the conductor and the shield of the cable.

In measurements effected on human beings, said sources of error may be eliminated by a selection of suitable cables, careful movements and a re-calibration.

But systems having no cables or only few and short cables are of special significance for veterinary diagnosis, in which relatively long cables must otherwise often be used.

In a suitable embodiment of the apparatus in accordance with the invention, particularly for an examination of animals, the housing of the sensing body together with the electrode and a shield, which may have a larger or smaller thickness and may be attached in various ways, is fixedly or pivotally or detachably mounted on a housing which contains the transmitting and receiving sections whereas there are no cables connecting the transmitting and receiving sections to the sensing body.

In that embodiment the transmitting electrode is connected to a cable and has a contact surface that is provided with pointed tips, humps or other elevations.

The transmitting electrode is suitably provided with means for a fixation to the body to be examined, such as belts or cords extending through holes, or Velcro fasteners.

Advantages will also be afforded by a separation of the transmitting and receiving sections because in that case said sections will not influence each other as will be the case if they are accommodated in a common housing. In case of such separation it will be possible to use components which otherwise could be shielded from others only with difficulty. Moreover, it will then be possible to use two power supplies, such as storage batteries, each of which may be small so that commercially available products may be employed. It will also be possible to use a common power supply, of course.

The transmitting section is preferably provided on one or more sides with outwardly facing metallic or other conductive parts, which are optionally provided with humps or other elevations for making contact with the skin of the animal.

For an examination of animals the transmitting section of the system is suitably encapsulated to a large extent for protection against dirt and moisture and also to permit it to be cleaned more easily; such cleaning will be necessary in any case because a contact gel is employed.

If a separate transmitting section is used in human medicine, that section may be attached to a suitable portion of the body to be examined, e.g., by a strip provided with a Velcro fastener.

If it is desired to separate the transmitting and receiving sections, said two sections will have a common ground (ground potential source) and that source will also be connected to the shields of the electrodes which are employed. This will be essential for an achievement of stable measured values if the transmitting and receiving sections are separate. For this reason, in a suitable embodiment of the apparatus in accordance with the invention the radio-frequency transmitting section and the radio-frequency receiving section are accommodated in separate housings and the same ground potential as the shields provided on the sensing bodies is applied to both sections because the two grounded parts are interconnected.

In a suitable embodiment of the apparatus in accordance with the invention the receiving section is provided with a fixed or movable and preferably rotatable sensing body, which is preferably provided with a housing for the more or less shielded electrode.

In another desirable embodiment of the apparatus in accordance with the invention the electrode, which is more or less shielded and is preferably contained in a housing, is connected by a cable to the radio-frequency receiving section.

A significant further development of the invention relies on a novel mode of modulating radio-frequency oscillations. The result which will be described hereinafter was not produced by the mere replacement of tubes by transistors. Only the use of field effect transistors which are controlled at their gates to provided a variable resistor permits a modulation of as much as 100% without a generation of harmonics. That operation will result in a very low background noise and will preclude cross modulation. As a result, the previously existing need for a re-calibration of the apparatus at the relative point of reference of the body to be examined is hardly required. In a particularly desirable embodiment of the apparatus in accordance with the invention, field effect transistors which are controlled at their gate to provide a variable resistor are associated with the apparatus as means for modulating the radio frequency in the transmitting section.

In another desirable embodiment of the apparatus in accordance with the invention, conductive contacts, which are fixed or displaceable, are provided over the shield and are insulated from the shield and from each other and/or from the outside and are adapted to be connected to sources of low electric potentials.

The remarks made hereinbefore in connection with the insulation of the shield in all suitable embodiments are logically applicable also to the insulation of the conductive contacts.

In a modification of that embodiment the conductive contacts are adapted at one end to contact the body to be examined.

The shield may be adapted to be disconnected.

The conductive contacts are desirably connected to indicating means for automatically indicating the position in which the apparatus is applied. A low electric potential is applied to each of the conductive contacts, which may consist of conductive strips, and different low electric potentials are suitably applied to respective ones of said contacts. The leads connected to said contacts, which are suitably spaced around the head of the sensing body, are connected in a certain sequence, in the clockwise or counterclockwise sense, to the indicating means, which particularly consists of a system for the acquisition of data (computer). The sensing body is suitably provided with a mark at a certain location so that the sensing body will always be applied in a certain position, e.g., with the mark facing upwardly. If the sensing body is applied in an incorrect, inclined position to the body to be examined, the body to be examined will make contact only with some of the contacts and only said contacts will be recorded by the data acquisition system and will be displayed on the screen. Even if the same potential is applied to the conductive contacts will it be possible to see whether the sensing body is applied in a correct or incorrect position and, in case of an incorrect position, the defined sequence of the contacts will furnish an indication of the side to which the sensing body is inclined. That side will also be apparent from an indication of different potentials applied to the contacts. As a result, the operator will see immediately that data are not obtained from all contacts which are spaced around the head of the sensing body and he or she will then correct the position of the sensing body until an indication is furnished that data are obtained from all contacts; this will be the case when the sensing body is applied at right angles. In the system for the acquisition of data the means for collecting and recording data may be so arranged that the measured data for the diagnosis will not be recorded unless the sensing body is applied at right angles so that a contact is made by all contacts and wrong data will automatically be blocked. It will be understood that that modification of the apparatus in accordance with the invention can also be used when a data acquisition system is not provided. In that case the transmitted data may be delivered, e.g., to light-emitting diodes, which may be provided in an annular array on the front plate of the apparatus and which by their active or inactive state will indicate whether or not the sensing body is applied at right angles. For instance, a shining of all light-emitting diodes—or in another circuitry, an inactive state of all light-emitting diodes—will indicate an application at right angles. But a shining of only a few light-emitting diodes will indicate that the sensing body is applied in an incorrect, inclined position so that wrong measured values would be obtained for the diagnosis.

In the just described modification of the apparatus in accordance with the invention the conductive contacts are provided on the outside surface of the sensing body closely behind the ring, edge or other boundary of the shield, when viewed from the tip of the sensing body. An insulating layer is provided between the shield and the conductive contacts and may consist of air. The contacts are also insulated from each other.

In another modification of the embodiment just described the conductive contacts constitute also a shield. In that case the low potentials applied to said shielding conductive contacts, e.g., potentials of 2, 4, 6, 8 and 10 volts, may effect a leakage or shielding like a ground potential. If contacts consisting, e.g., of contact strips, are very closely spaced apart they will substantially prevent a radiation onto the receiving electrode. In that case a leakage of the radio-frequency energy will be effected by the contact with the metallic or metallized edge or other boundary of the conductive contacts when an adequate contact pressure is applied (spontaneous leakage) and owing to the contact which is made an indication will be given as described whether the sensing body is applied at right angles.

In a still further modifications of the just described embodiment of the apparatus in accordance with the invention, shields may be provided which are disposed inside the housing of the sensing body and are displaceable outwardly and the pressure applied may be defined in that the forward portion of the head of the sensing body or the conductive contacts which are externally disposed are adjustable and it is desired to form on the body to be examined a depression in different depths in dependence on the region of the body to be examined and on the hardness of the tissue. When the distance has been adjusted and a depression in a predetermined desired depth has been formed, that fact will be indicated by the indicating means, e.g., in that the diodes are shining. The measured value can then be read. In that case all measurements taken with depressions having the same depth will be reproducible and will furnish identical measured values if they are taken at the same location and at the same time of the day and under the same ambient conditions.

In a still further modification of the above-described embodiment of the apparatus in accordance with the invention the conductive contacts are provided on the outside of the housing of the sensing body or in the wall of said housing and the shielding means comprise or exclusively consist of said contacts. The conductive contacts may be displaceably mounted in the housing so that only their forward portions are selectively displaced out of the sensing body through slots or may be concealed in the housing. Various modes of operation may selectively be employed: When the conductive contacts have been retracted so that they are concealed they may serve only as a shield. When they have been pushed out to a smaller or larger extent the edges of the conductive contacts may additionally contact the body to be examined for a leakage of the radio-frequency energy so that the pressure applied can be indicated and the peak values can automatically be recorded. If the contact strips do not effect a shielding and are merely connected in a predetermined sequence to an indicating or recording apparatus, the contacts will be used only for providing an indication of the position in which the sensing body is applied (either in an incorrect, inclined position or in a correct position at right angles). The two modes of operation mentioned last may be combined.

The measured values may be indicated by a pointer instrument or by other means, e.g., by a digital display or, as has been mentioned hereinbefore, by means of an apparatus for recording measured data (computer).

Medical diagnosis may also be used to detect the effects of medicaments which have been administered. If the medicaments exhibit an activity in certain local regions or organs, the measured values will differ in many cases from those obtained without therapy. The measured values will also change as the therapy proceeds so that measured values which progressively approach normal values will suggest an improvement whereas measured values which progressively depart from normal values will suggest that the medicaments are ineffective.

"Passive electric four-terminal networks" are known in the art and have been embodied in innumerable electric circuits. But such networks have not been used thus far for medical diagnosis and owing to the special conditions and requirements mentioned hereinbefore the use of the passive four-terminal network in the apparatus in accordance with the invention is of high significance because it will permit only those changes to be detected which have taken place at a defined location relative to the calibration location and which reflect the inhomogeneities to be detected.

A combination of features of various suitable embodiments of the apparatus in accordance with the invention will result in a cumulation of the associated advantages so that particularly excellent results can be produced.

BRIEF DESCRIPTION OF THE DRAWINGS

Illustrative embodiments of the invention will now be explained more in detail with reference to the drawing. In any embodiment in which an insulation is not shown on a shield, such insulation may nevertheless optionally be provided. Besides, any embodiment may comprise a shield (not shown) which is disposed within a housing wall. Moreover, any embodiment may comprise one or more shields of conductive material whereas a housing is not provided.

In all figures of the drawing the sensing bodies are shown in longitudinal section unless stated otherwise.

FIGS. 1 and 2 illustrate a sensing body for detecting properties of a body to be examined.

DETAILED DESCRIPTION OF THE PREFERRED EMBODIMENTS

Figure 3:
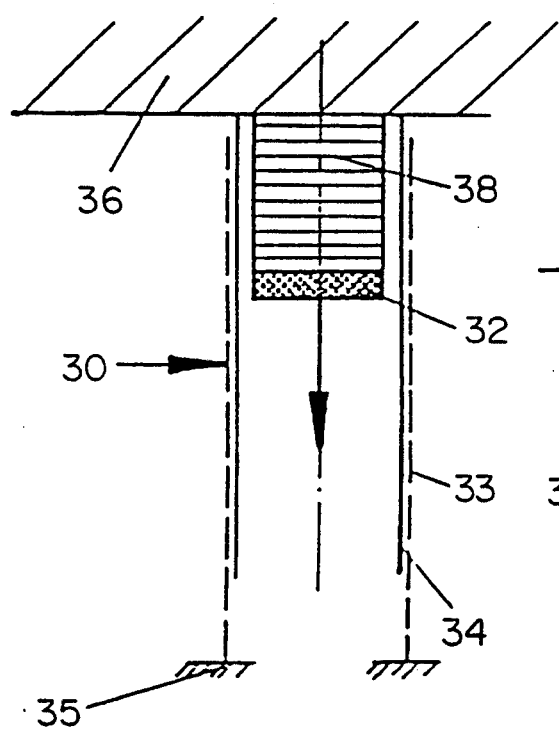
FIGS. 3 and 4 illustrate a sensing body which includes an electrode accommodated in a housing.

FIG. 1 shows a sensing body 80 for detecting properties of a body to be examined. The sensing body comprises a housing 82 and an electrode 86 disposed within the housing. The electrode 86 is connected by a lead 87 to a measuring device, not shown. In the embodiments shown in the other figures of the drawing that lead is provided for the same purpose but is not designated by a reference number. The end of the housing 82 of the sensing body 80 is applied to a body 88 of a human or animal to be examined. The selectable distance between the surface of the body 88 and the electrode 86 is designated a. A shield 84 connected to a ground lead 85 is mounted on the side wall of the housing 82.

The embodiment shown in FIG. 2 is like that shown in FIG. 1 with the only difference that an insulation layer 89 is provided on the shield 84.

FIG. 3 shows a sensing body 30 which comprises an electrode 32 that is accommodated in a housing 34. The end face 34 of the housing contacts a body 36 of a human or animal that is to be examined. The space between the surface of the body 36 and the electrode 32 is filled with a deformable material so that the distance from the electrode 32 to the surface of the body 36 can be changed by a laterally applied pressure. For instance, air may be admitted to the space between the material 38 and the housing 34. A shield 33 connected to a ground lead 35 is also provided on the side wall of the housing 34.

Figure 4:
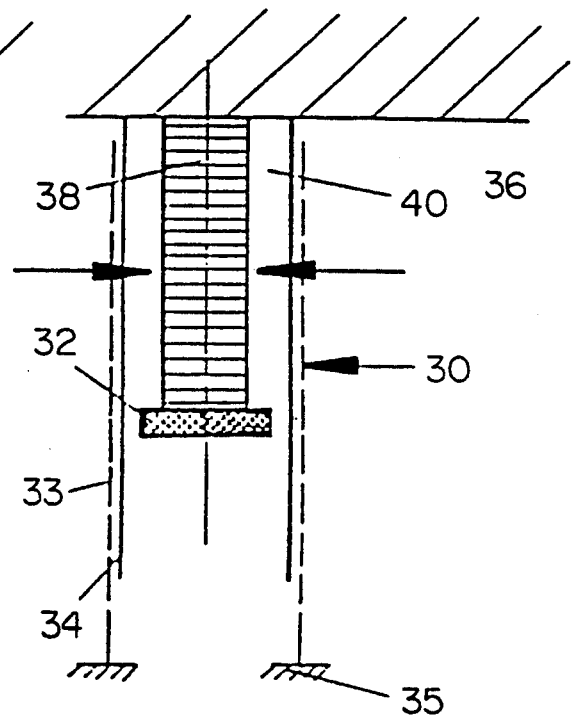

FIG. 4 shows the sensing body 30 of FIG. 3 with the material 38 compressed. The space 40 between the deformable material 38 and the wall of the housing 34 has been compressed so that the electrode 32 has been displaced to the rear in the housing 34 and the distance between the electrode 32 and the surface of the body 36 has been increased.

Figure 5:
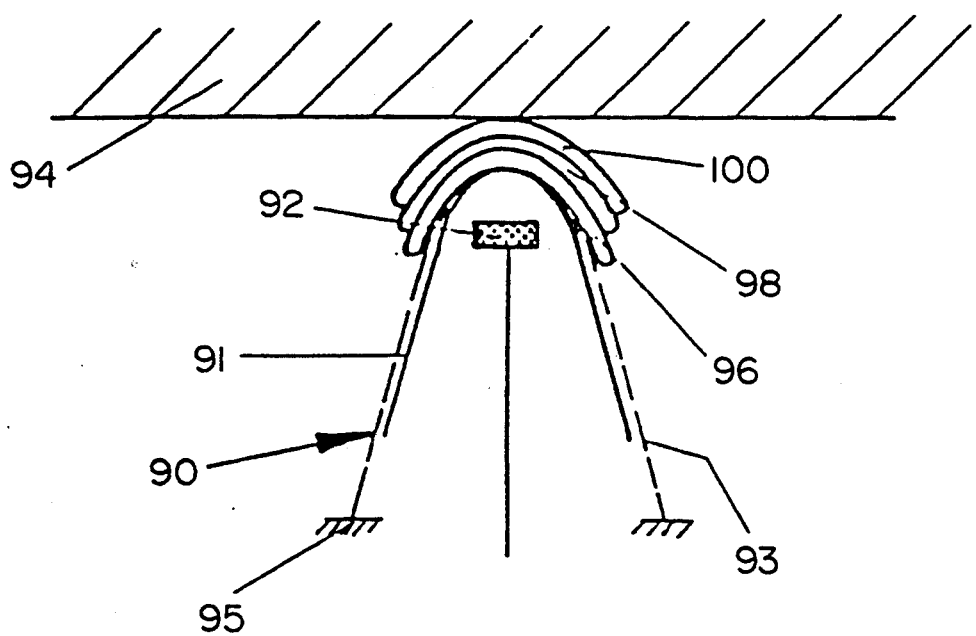
FIG. 5 illustrates a sensing body which includes an electrode contained in a housing.

FIG. 5 shows a sensing body 90 which comprises an electrode 92 contained in a housing 91. To permit a change of the distance from the electrode 92 to the surface of the body 94 that is to be examined, spacer shells 96, 98, 100 may be provided, which can simply be laid one over the other and by their presence may selectively change the value measured by the electrode 92. A shield 93 is provided on the side wall of the housing 91 and is connected to a ground lead 95.

Figure 6A:
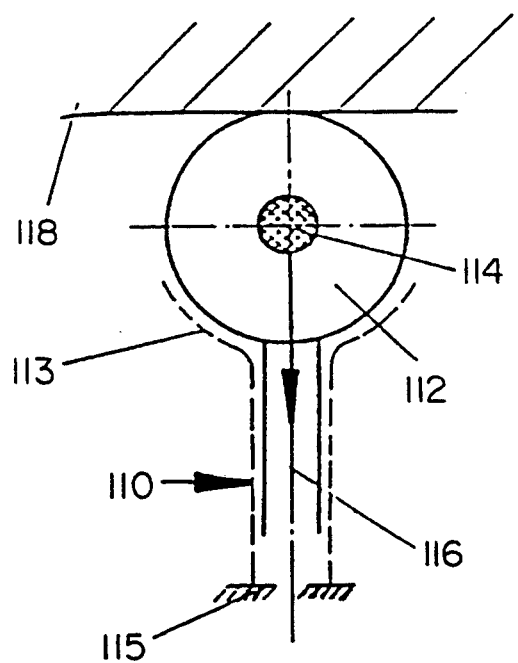
FIGS. 6a, 6b and 7 illustrate sensing bodies which include a spherical housing that is made of a material having a suitable dielectric constant.
Figure 6B:
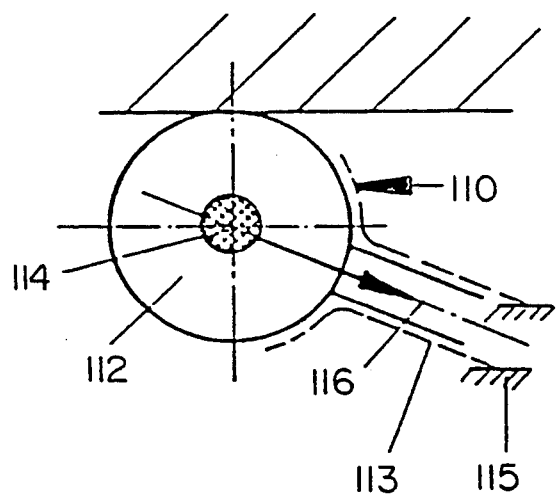
Figure 7:
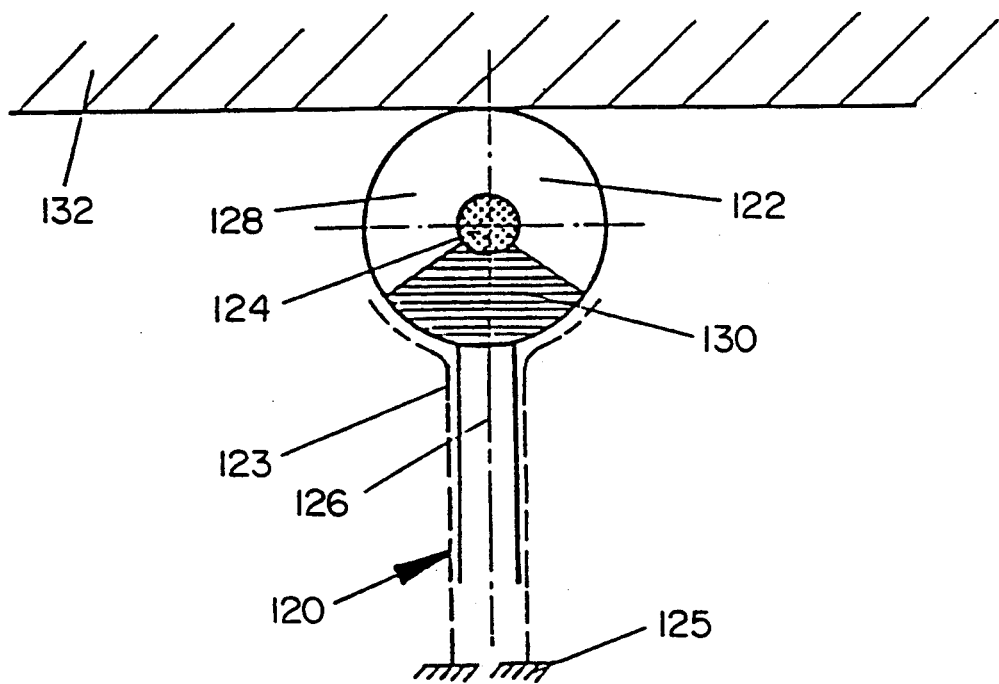

FIGS. 6 and 7 show sensing bodies 110 and 120, respectively, which comprise a spherical housing 112 or 122 that is made of a material having a suitable dielectric constant. The spherical housing 112 contains an electrode 114. The spherical housing 122 contains an electrode 124. The sensing body 110 or 120 is provided with a handle rod 116 or 126 for handling the sensing body 110 or 120. In the sensing body 110 the spherical housing 112 consists entirely of the same material. In the sensing body 120 the spherical housing 122 consists of two materials, namely, a material 128 and a material 130 which is disposed in one sector. Said materials may have different dielectric constants. The spherical shape of the housings 112 and 122 which enclose the electrodes 114 and 124, respectively, ensures that even if the sensing body is tilted or rotated as it is moved over a body 118 or 132 that is to be examined the distance from the electrode 114 or 124 to the body to be examined will always be the same. A shield 113 or 123 connected to a ground lead 115 or 125 is provided on the periphery of the spherical housing 112 or 122.

Figure 8:
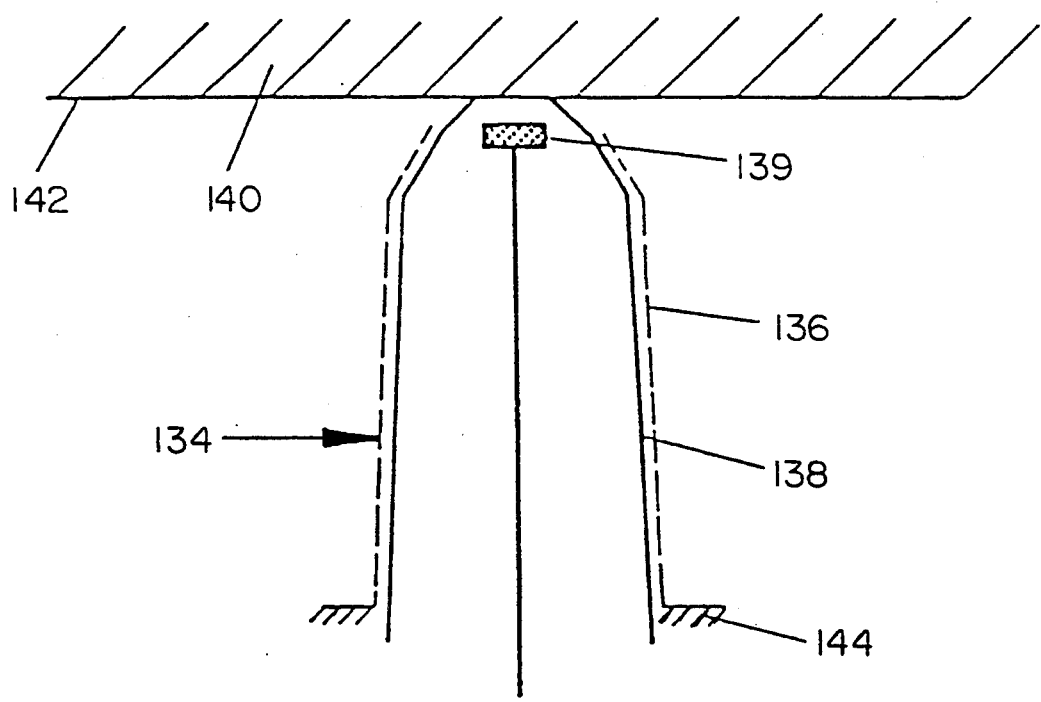
FIGS. 8 and 9 illustrate a sensing body including an electrode disposed in a housing and a metallic shield which is provided on the outside of the housing and which is connected to a ground lead.

FIG. 8 is a diagrammatic view showing another embodiment of a sensing body 134 comprising an electrode 139, which is disposed in a housing 138 and a metallic shield 136, which is provided on the outside of the housing 138 and is connected to a ground lead 144. That shield may consist of conductive silver paint. In that embodiment the contact of the shield 136 with the skin 142 in response to the application of a high pressure to a soft portion 140 of the body will result in a sudden drop of the value which is measured by the measuring instrument because the energy of the radio-frequency field is dissipated to ground at 144. The drop of the measured value will indicate that an excessively high pressure has been applied and the conditions are not the same as at the calibration point (not shown in FIG. 8), at which the sensing body 134 had been impressed before to such a depth that a peak value was measured before the shield was contacted by the body to be examined.

Figure 9:
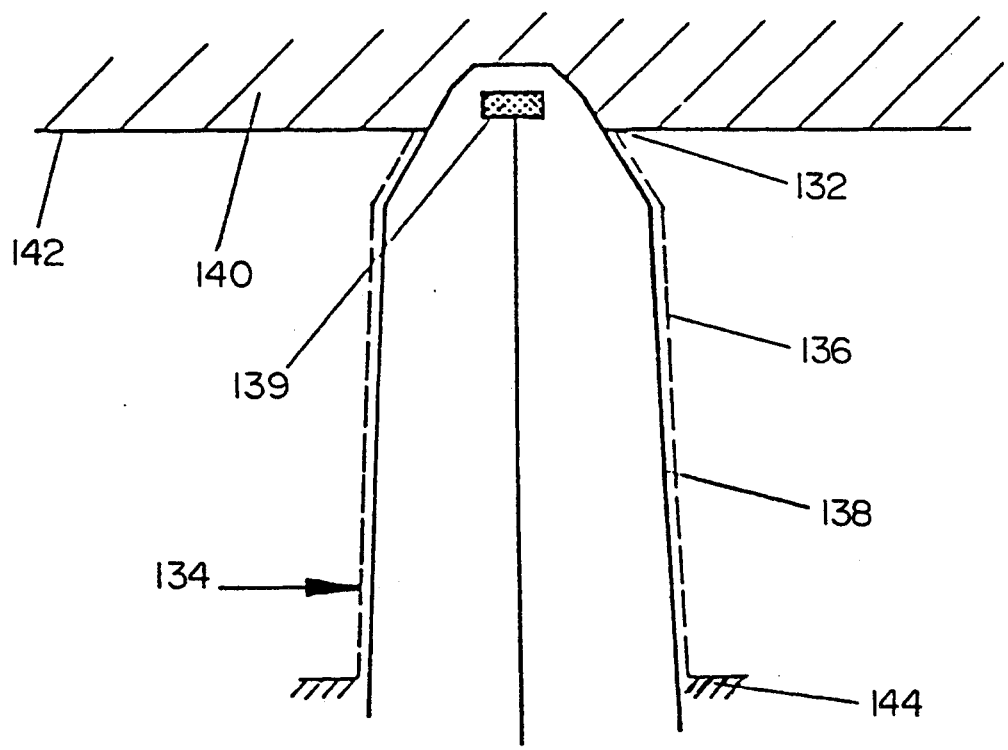

The sensing body shown in FIG. 8 is shown in FIG. 9 in a position in which the skin 142 of the body to be examined is contacted at 132 by the shield 136.

Figure 10:
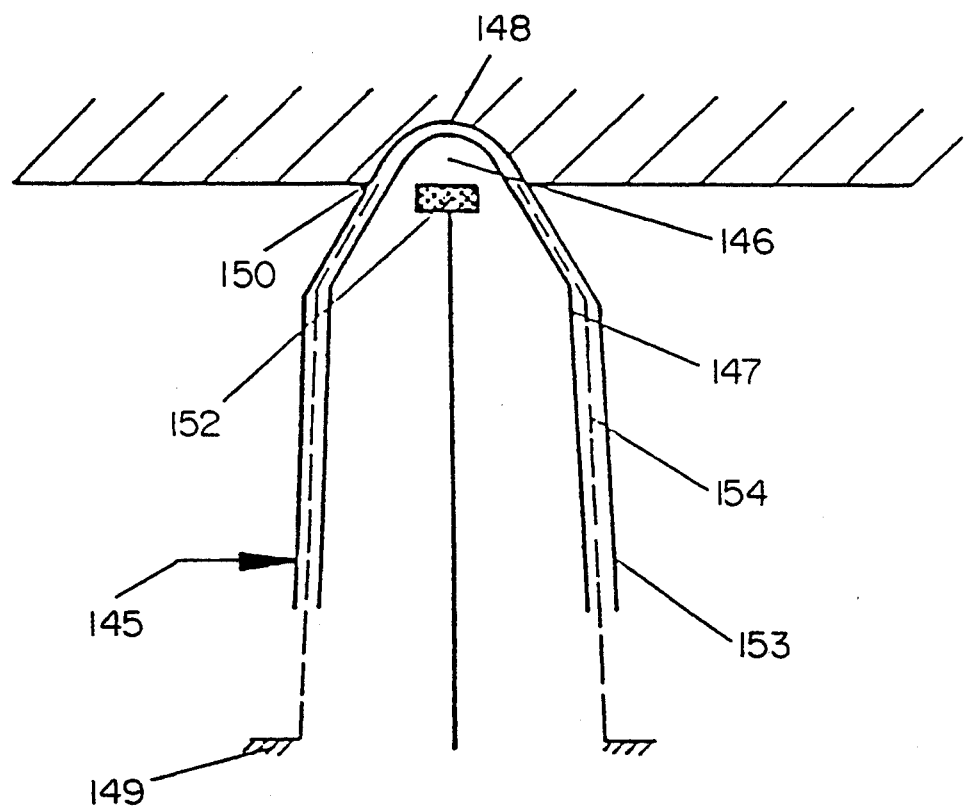
FIG. 10 illustrates a sensing body having a housing provided with a shield made of conductive material applied to the outside of the housing and connected to a ground lead.

FIG. 10 shows an embodiment of a sensing body 145 having a housing 147, which is provided with a shield 154 consisting of conductive material applied to the outside of the housing 144 and is connected to a ground lead 149. An insulation 153 is provided on the shield 154 and increases or decreases in thickness toward the tip of the sensing body and is so designed that the forward edge of the shield 154 disposed under the insulation 153 will not be able to make conductive contact with the body to be examined and by such contact to dissipate the energy of the radio-frequency field. In that embodiment, the material of the housing 147, the material and the shape of the space 146 between the electrode 152 and the point 148 where the skin is contacted by the sensing body 145, the thickness and density of the conductive material which constitutes the shield 154 are so selected in view of the results of experiments that the increase of the radiated field energy which would be received by the electrode 152 owing to the depression formed in the skin 150 of the body to be examined will be compensated by a change of the effect of the shield 152 in such a manner that almost the same measured values will be indicated by the indicating instrument. The shield 154 may be provided, e.g., on the outside of the forward portion of the housing 147 and may be insulated and may be continued in the wall of the housing 147 or in the interior of the housing 147. All materials and shapes and the distance between the electrode 152 and the point 148 where the body to be examined is contacted must be selected for their specific qualities (also in dependence on their different dielectric constants) so that said compensation will be effected.

Figure 11:
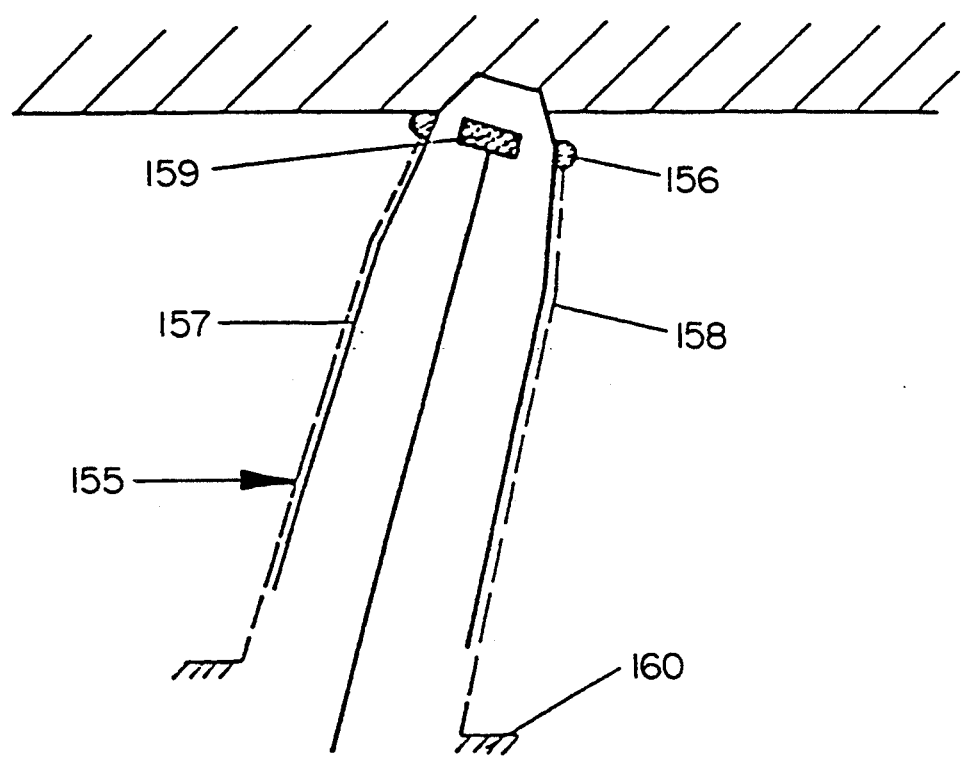
FIG. 11 illustrates a sensing body in which an electrode is contained in a housing.

FIG. 11 shows a different embodiment comprising a sensing body 155 in which an electrode 159 is contained in a housing 157. The sensing body 155 is provided with a metal ring 156, which is disposed, e.g., at that point of the housing 157 at which the metallization terminates in FIGS. 8 and 9. That ring 156 is also connected to ground 160 by a lead 158, which may optionally act also as a shield. In that embodiment, a canting (application of the sensing body to the skin in an inclined position—as is shown here) or an impression on the tissue to an excessive depth will result in a fast and reliable leakage of the radio-frequency energy to ground 160 so that the drop of the value indicated by the pointer of the measuring instrument (or by a numerical indication of a digital instrument) will be particularly conspicuous and the operator will be immediately aware that the measurement is not correct. Owing to the provision of the means shown by way of example in FIGS. 8, 9 and 11 for a leakage of the radio-frequency energy to ground it is unexpectedly and desirably possible to transmit to a data memory and data processor (computer, display screen, plotter) those measured data which represent the peak value of a measurement and have been obtained immediately before the decrease of the excursion of the pointer. This will decisively simplify the handling during the measurement and will result in a measuring of reproducible values if the apparatus has been handled in the same manner for a calibration at a reference point of the body to be examined.

Figure 12:
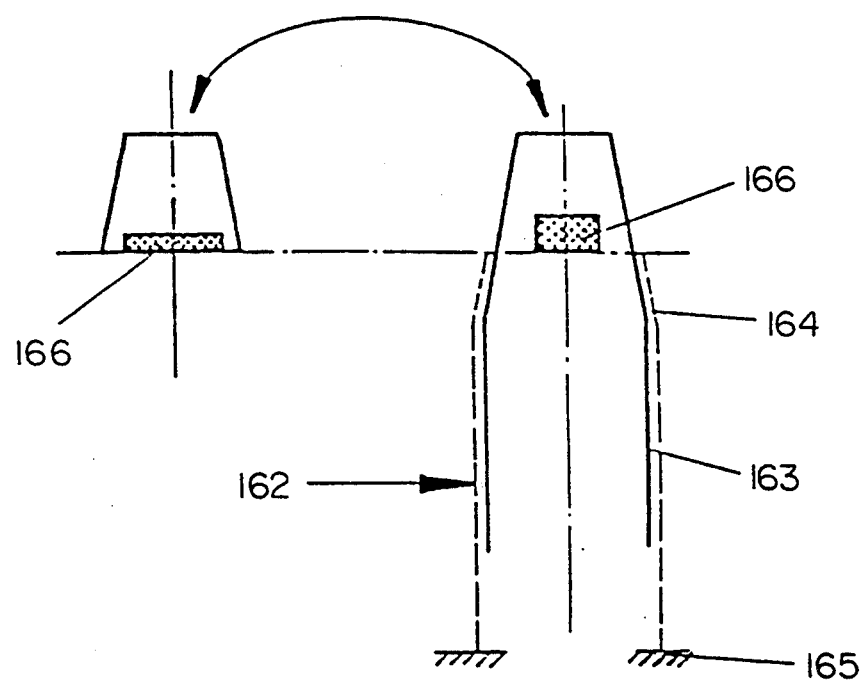
FIG. 12 illustrates a sensing body including an electrode that is disposed in a detachable part of a housing.

FIG. 12 diagrammatically shows a further embodiment of a sensing body 162 comprising an electrode 166 that is disposed in a detachable part of a housing 163. That housing part can be replaced by different housing parts which contain electrodes 166 differing in shape and/or size so that a higher or lower sensitivity to the field strength can be preselected. A shield 164 connected to a ground lead 165 is provided on the housing and will have different effects if different detachable housing parts are employed.

Figure 13:
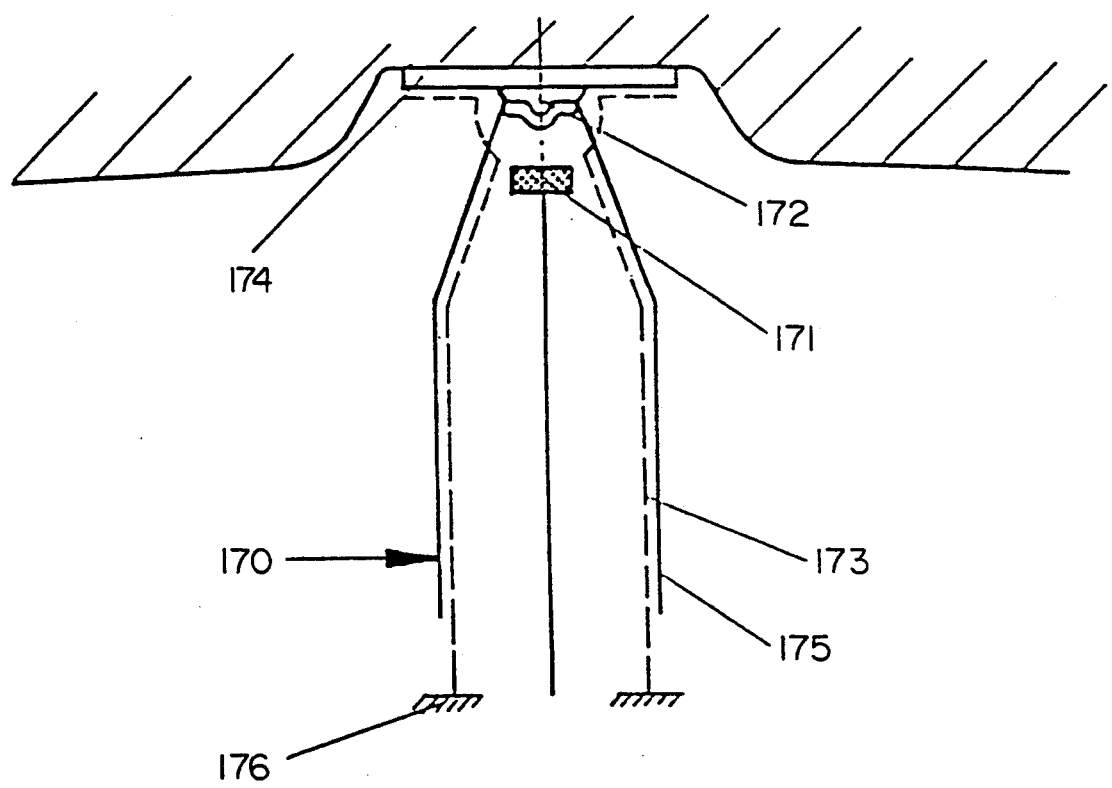
FIG. 13 illustrates a sensing body in which an electrode is disposed in a housing.

FIG. 13 shows another embodiment comprising a sensing body 170, in which an electrode 171 is disposed in a housing 175. The housing 175 is provided at its tip with a flexible disk 174 (or with a member having a different configuration, e.g., of a quadrangle), which is attached preferably by a snap fastener joint 172 although a different adhesive joint may be used. A plurality of such disks in different sizes may be provided for a replacement. A shield 173 that is connected to a ground lead 176 is provided and extends on the rear surface of the flexible disk 174 and on the outside surface of the housing 175 and is continued on the inside surface of the housing 175. If that design is adopted and the material of the disc 174 has properly been selected to have the lowest possible dielectric constant, it will be possible to avoid undesired lateral influences which might be due to deformed surface portions of the body to be examined and might result in an incorrect increase of the field strength which is received. The disk 174 may be made of different materials, i.e., it may be composed of different materials having different dielectric constants so that the radio-frequency energy which is radiated onto the receiving electrode 171 will be channeled. The sensitivity for radio-frequency energy may be controlled by the provision of shields 173 which differ in dimensions and arrangement.

Figures 14A, 14B:
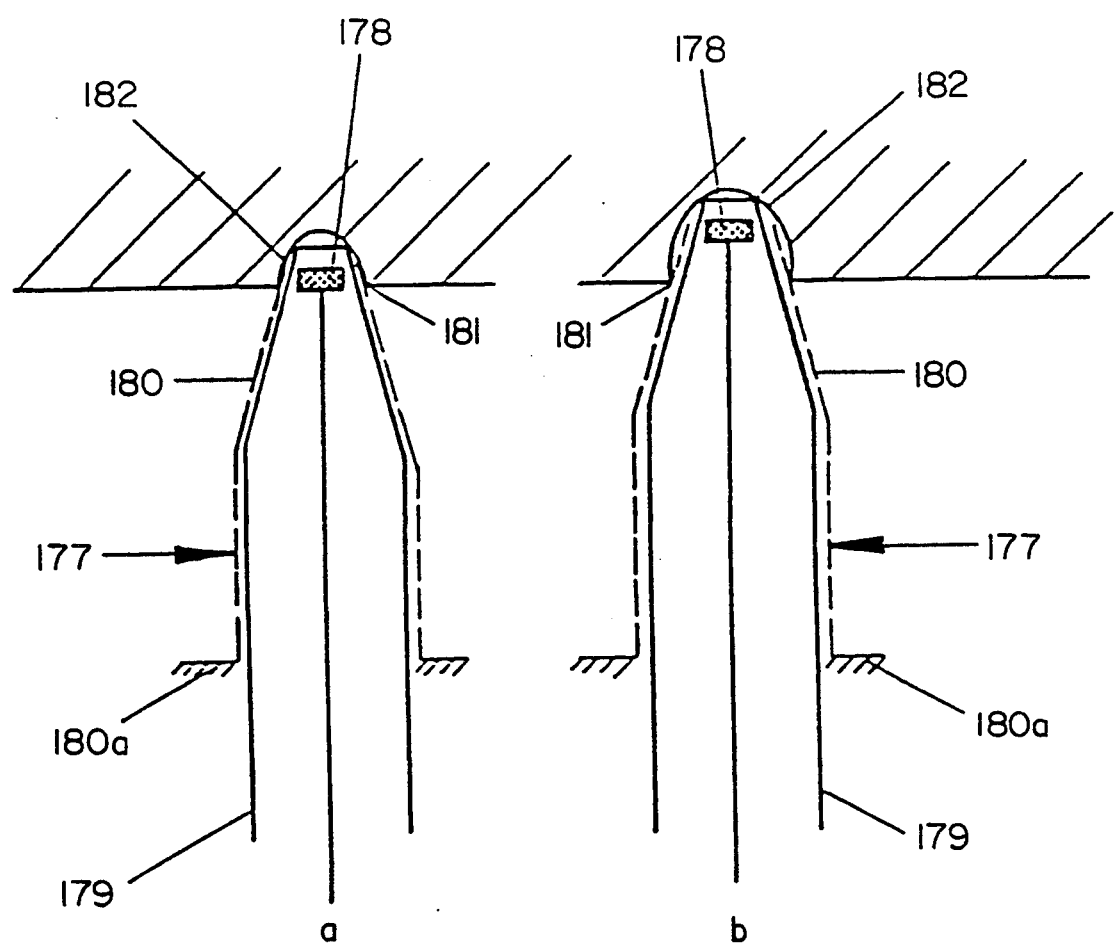
FIGS. 14a and 14b each illustrates a sensing body in which an electrode is contained in a housing, which is provided with a shield made of conductive silver paint.

FIG. 14 shows a further embodiment comprising a sensing body 177, in which an electrode 178 is contained in a housing 179, which is provided with a shield 180 consisting of conductive silver paint. The boundary or edge 181 of the metallic or metallized surface is adapted to contact the skin for a spontaneous dissipation of the radio-frequency energy via the shield 180 to ground 180a and the location of said boundary or edge 181 can be varied in that the tip of the sensing body is provided with insulating caps 182 which differ in size.

Figure 15:
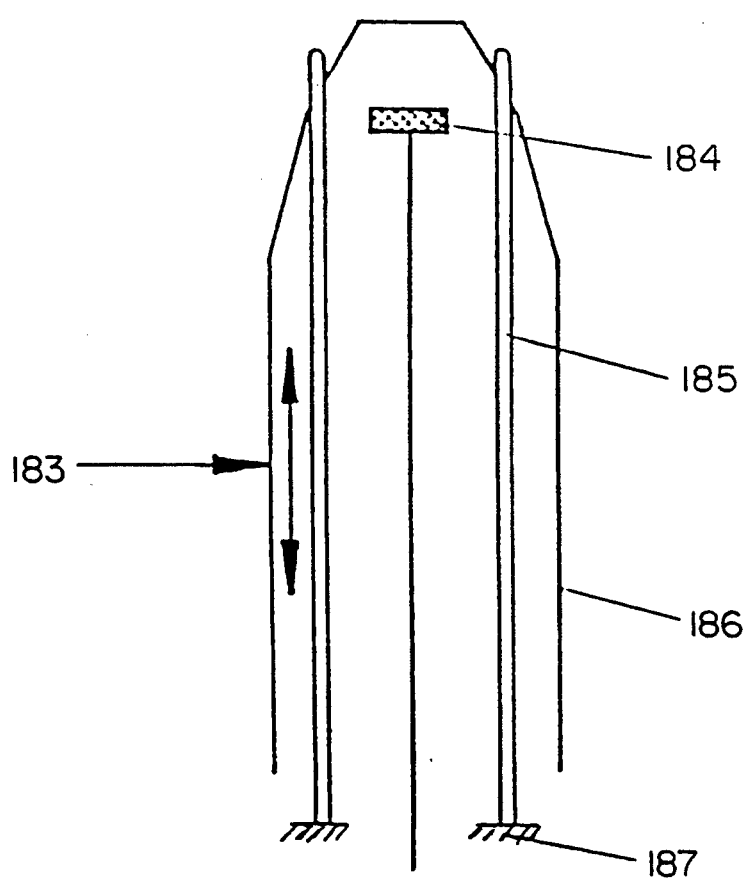
FIG. 15 illustrates a sensing body in which an electrode and a shield connected to a ground lead are contained in a housing.

FIG. 15 shows an embodiment comprising a sensing body 183 in which an electrode 184 and a shield 185 connected to a ground lead 187 are contained in a housing 186. The internally disposed shield 185 consists of a metal tube 185, which protrudes from the housing at its forward end and can be moved to the rear along its longitudinal axis. Alternatively, the metal tube may be fixed in the housing 186. Via the protruding metal tube 185 the radio-frequency energy can spontaneously be dissipated as in the embodiments shown in FIGS. 8, 9, 11, 12 and 14. The change of the position of the shield 185 will reduce or increase the capacitance.

Figure 16A:
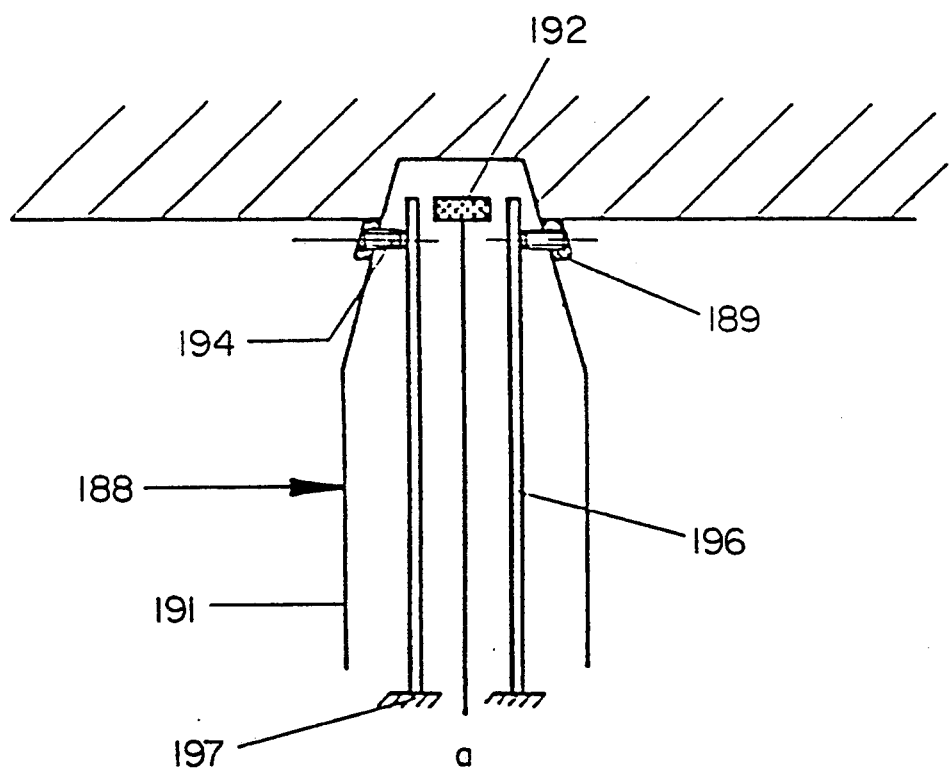
FIGS. 16a and 16b each illustrates a sensing body including an electrode that is contained in a housing and a shielding ring provided on the housing.
Figure 16B:
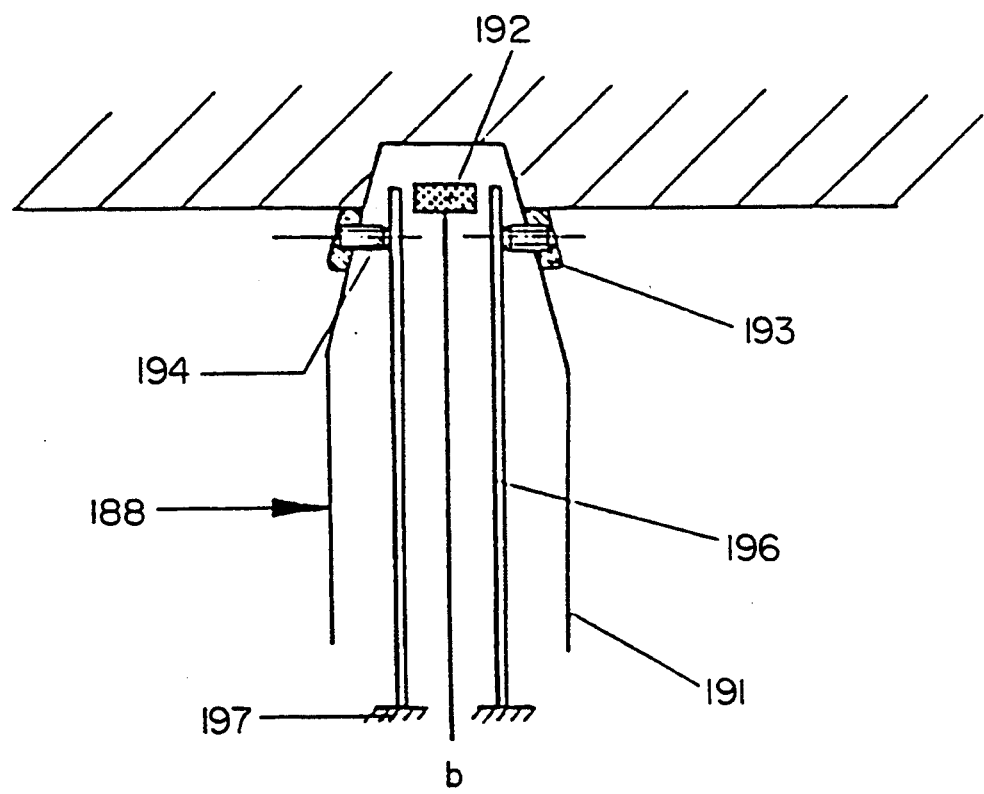

In the embodiment shown in FIG. 16 a sensing body 188 comprises an electrode 192 that is contained in a housing 191 and a shielding ring 189 provided on the housing 191. The ring 189 may be replaced by another shielding ring that has a larger or smaller rim 193. By means of electrically conducting headless screws 194 the ring 189 is connected to the internally disposed shield 196, which constitutes a continuation of the shield consisting of the ring 189, 193 and is connected to a ground lead 197. Instead of the internally disposed shield 196, a shield may be provided on the outside of the housing 191 or a shielding may be effected only by the ring 189, 193, which in that case will directly be connected to ground. A contact of the ring 189, 193 with the skin will produce the results which have been described with reference to FIGS. 11 and 15.

Figure 17:
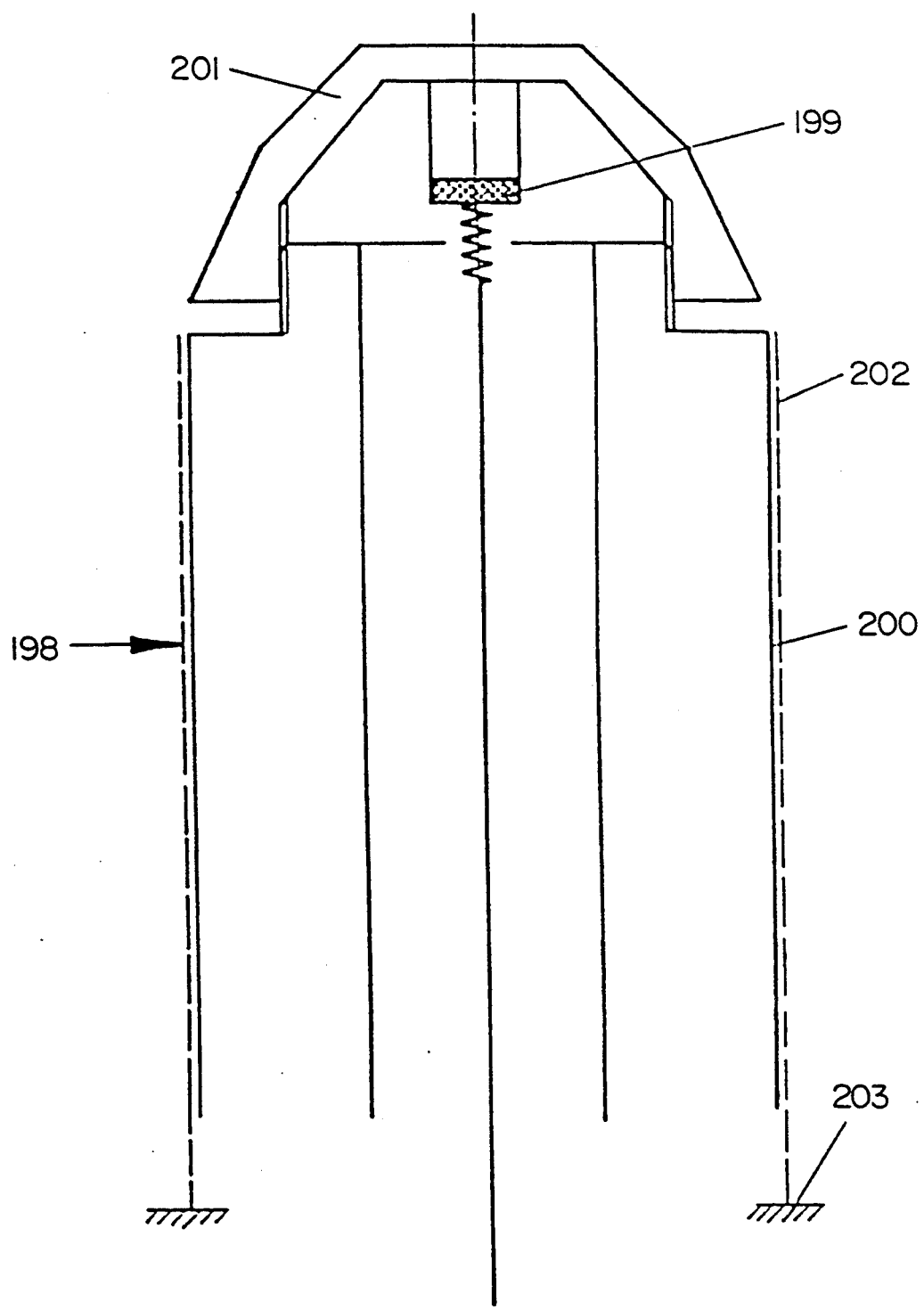
FIG. 17 illustrates an electrode which is contained in a housing.

FIG. 17 shows a sensing body 198 comprising an electrode 199 which is contained in a housing 200. The forward portion 201 of the housing 200 is displaceably or screwably mounted so that the effect of the shield 202, which is provided on the housing 200 and connected to a ground lead 203, can be changed.

Figure 18:
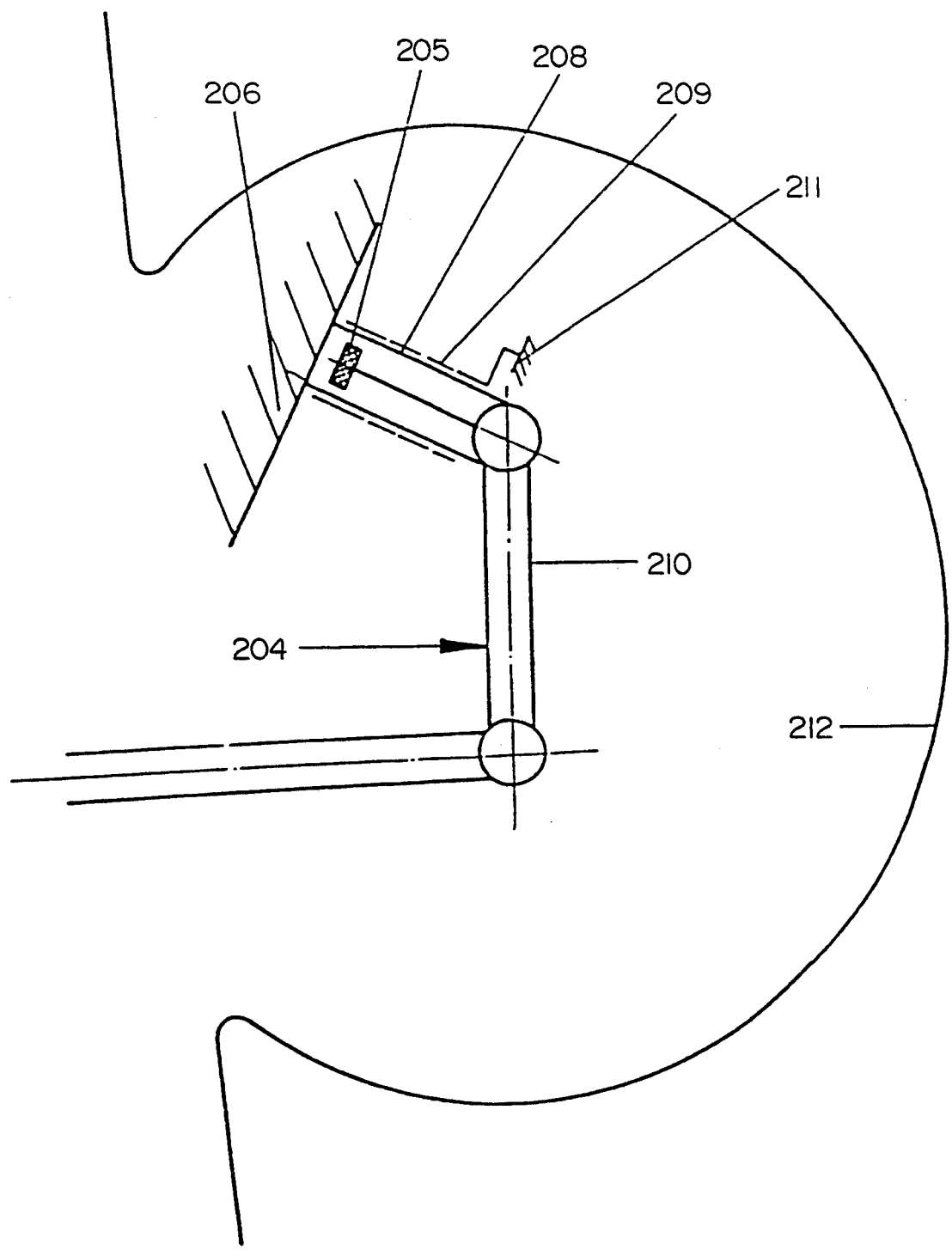
FIG. 18 illustrates a sensing body including an electrode in a housing having a forward part that is provided with a shield connected to a ground lead.

FIG. 18 shows a sensing body 204 comprising an electrode 205 in a housing which comprises a forward part 208 that is provided with a shield 209 connected to a ground lead 211. That sensing body can be used to examine gingiva 206 on the inside (or outside) or to examine another location in the throat 212. The forward part 208 and optionally also the rear part 210 is pivoted for permitting an access to difficulty accessible locations in the throat or of the gingiva while the forward part of the sensing body is held at right angles to the surface which is to be examined. This is necessary because an inclined position of the electrode may result in measuring errors in spite of the laterally disposed shield 209.

Figure 19:
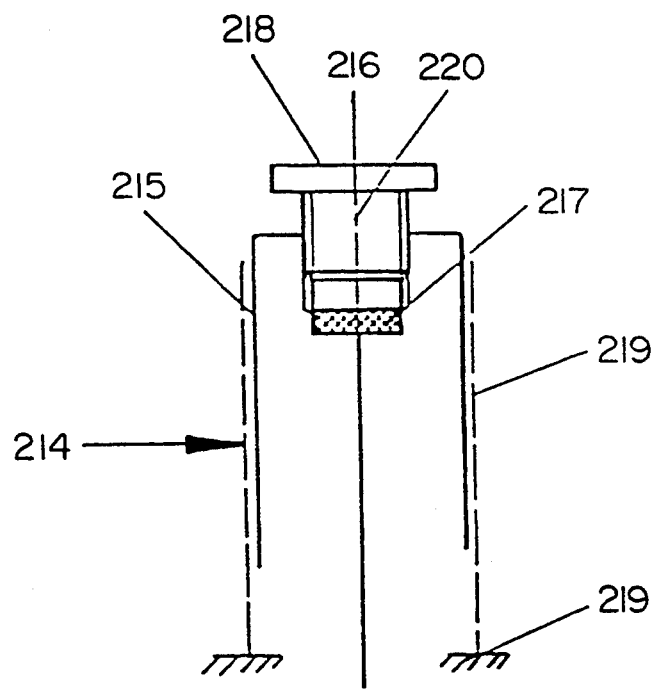
FIG. 19 illustrates a sensing body which includes an electrode, which is disposed in a housing that is provided at its forward end with an adjusting screw.

FIG. 19 shows a sensing body 214 which is intended, e.g., for an examination of the throat or the vagina and comprises an electrode 220, which is disposed in a housing 215 that is provided at its forward end with an adjusting screw 216, which preferably consists of plastic material and can be screwed into and out of the housing to change the distance between the contact surface 218 and the electrode 220. In dependence on the position of the adjusting screw 216 the effect of the shield will be larger or smaller. A shield 217 connected to a ground lead 219 is provided on the housing 215.

Figure 20:
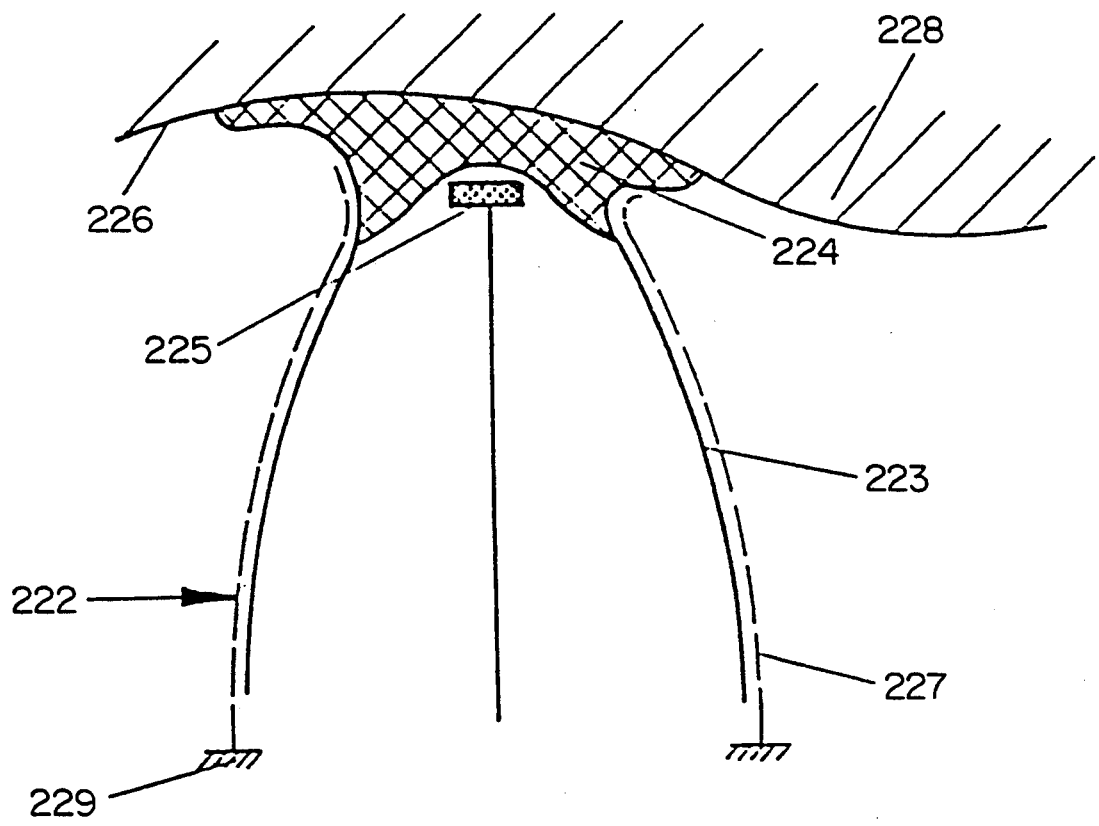
FIG. 20 illustrates a sensing body in which an electrode is contained in a housing which, in its forward part disposed in front of the electrode, is provided with an attached and optionally detachable member, deformable for adaptation to the surface of a body that is to be examined.

FIG. 20 shows a sensing body 222 in which an electrode 225 is contained in a housing 223, which in its forward part is disposed in front of the electrode 225 and is provided with an attached and optionally detachable member 224, which is deformable for adaptation to the surface 226 of the body that is to be examined in order to prevent an ingress of air between the surface 226 to be examined and the sensing body 222 (this would incorrectly reduce the measured value) and to prevent an impression of the sensing body into the body to be examined because such an impression would result in a compression of tissue 228 so that more field energy would be radiated from the tissue 228 in a lateral direction and the measured value would incorrectly be increased. Like the disk shown in FIG. 13 that deformable member may be composed of different materials. A shield 227 connected to a ground lead 229 is provided on the outside of the housing 223.

Figure 21:
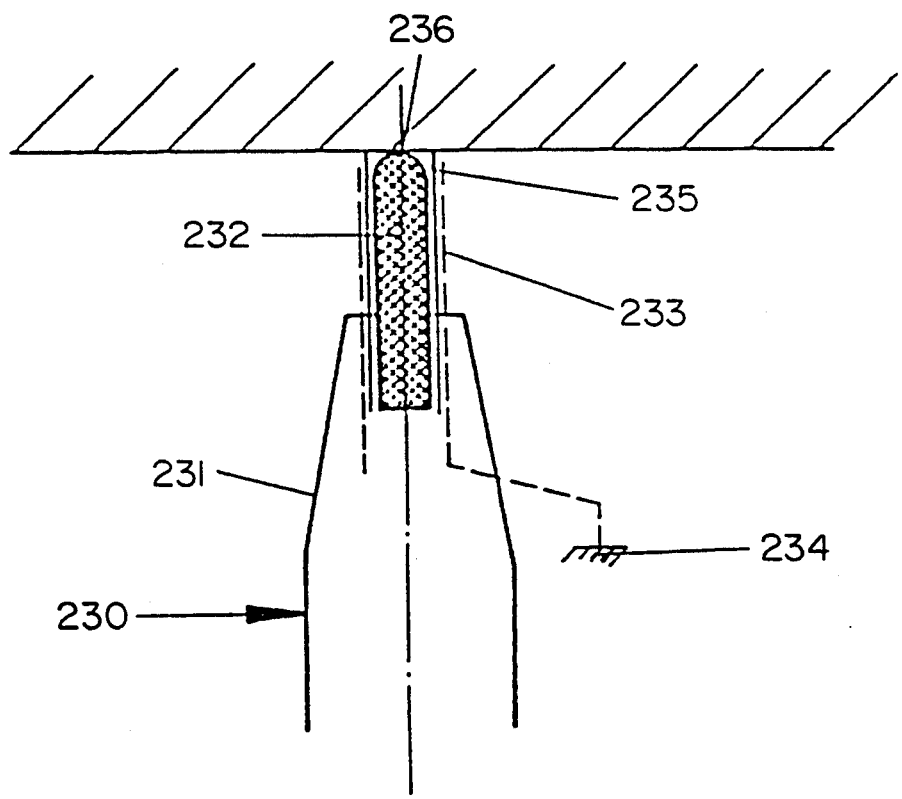
FIG. 21 illustrates a sensing body comprising a housing, an electrode, which protrudes in part out of the housing and is very closely spaced from the surface to be examined.

FIG. 21 is a diagrammatic representation of a sensing body 230 comprising a housing 231 and an electrode 232, which protrudes in part out of the housing and is very closely spaced from the surface to be examined. The electrode 232 is provided on the outside with a shield 233, which is connected to a ground lead 234 and is separated by an insulation 235 from the electrode 232. That sensing body 230 may be used for a satisfactory detection of acupuncture or neural points on the human or animal body without a fluctuation of the measured values. The small distance from the surface to be examined can be ensured, e.g., by a simple coat of paint 236. The shield 233 may also be provided with a protective coat of paint.

Figure 22:
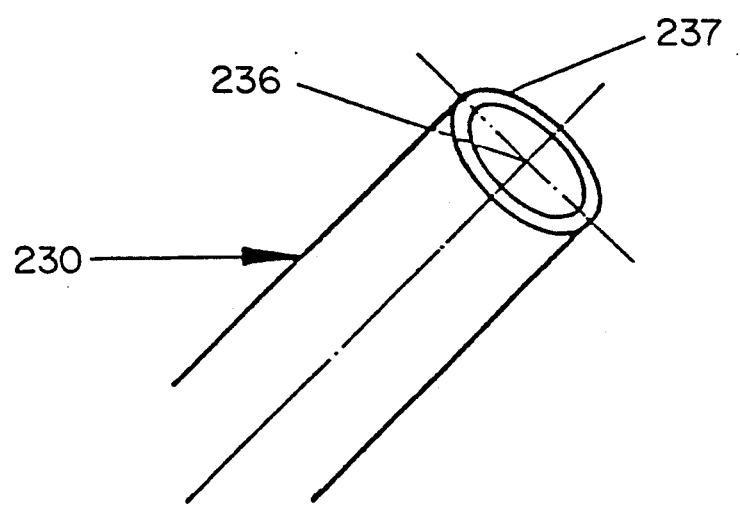
FIG. 22 illustrates a sensing tip of a sensing body shown in FIG. 21.

FIG. 22 shows the sensing tip 236 of the sensing body 230 shown in FIG. 21, which at said sensing tip is provided with a circular edge 237 (which edge may have any desired configuration). That edge 237 can be forced against the skin to indicate the acupuncture or neural point that has been detected by a mark which will last a few seconds. During that time an acupuncture needle or, e.g., a stick-on treating device which is commercially available can be applied exactly to the point which has been detected before so that the effect of the needle puncture or of the pressure of a material having no needlelike point and consisting, e.g., of metal, metallized plastic or another material for treating acupuncture or neural points will be optimized.

Figure 23:
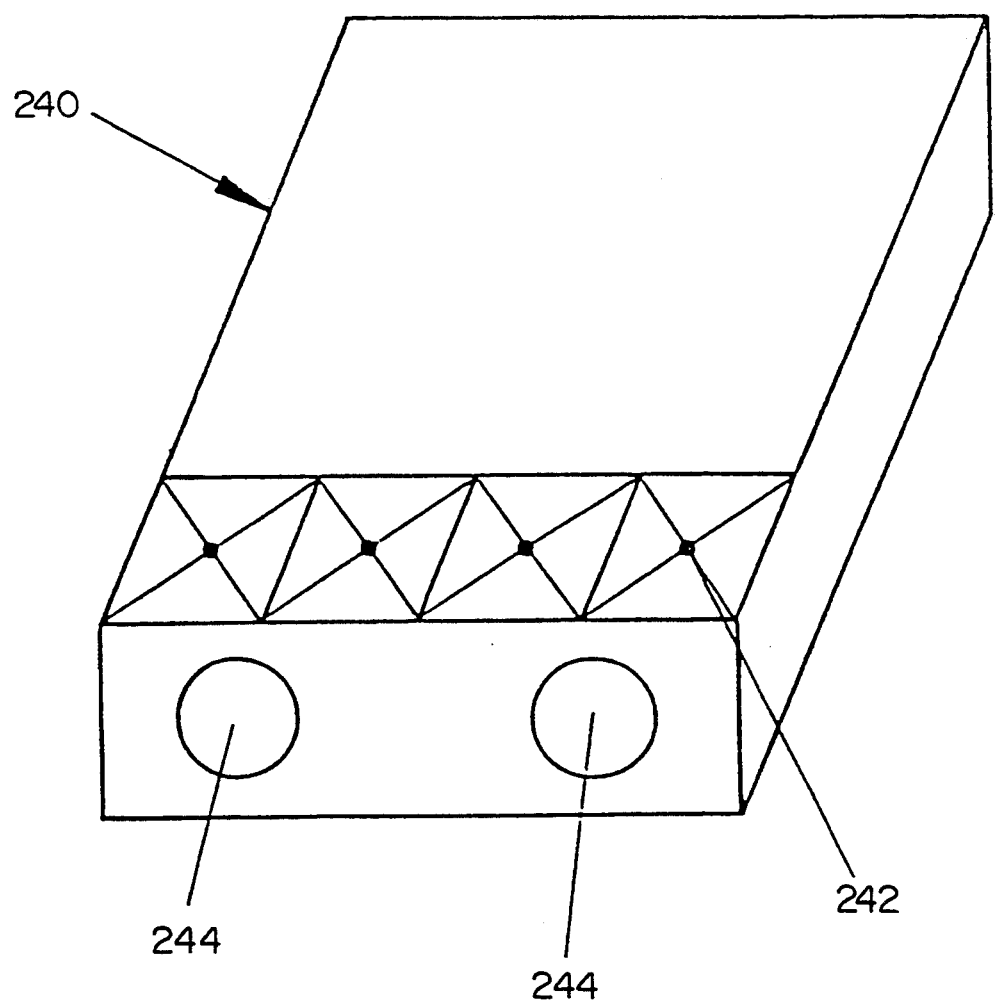
FIG. 23 illustrates a metallic transmitting electrode.

FIG. 23 shows a metallic transmitting electrode 240 in an embodiment intended, e.g., for an examination of animals so that the transmitting electrode 240 must be attached to the animal, for instance, with an adhesive fastener, e.g., a Velcro fastener or belts which extend through holes 244. The transmitting electrode is formed at its contact surface with protruding edges or pointed tips 242 or elevations having other shapes so that they will penetrate through hair on the skin of the animal, possibly with the aid of a contact-promoting gel, a highly conductive contact can thus be established.

Figure 24:
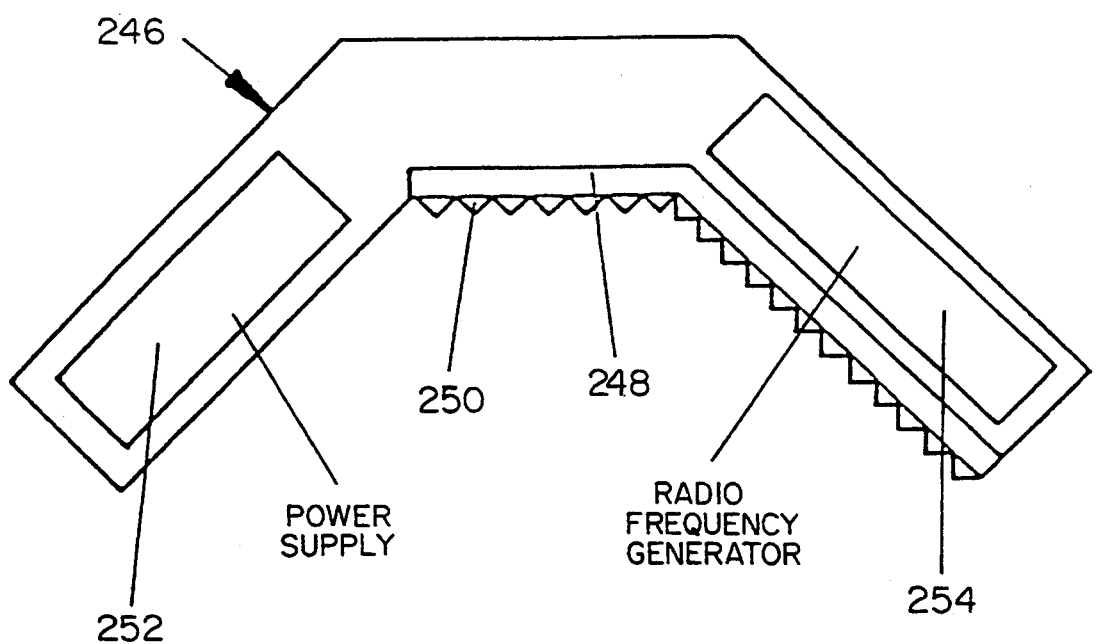
FIG. 24 illustrates a transmitting section including a power supply and a radio frequency generator.

FIG. 24 diagrammatically shows an embodiment of the transmitting section 246 comprising a power supply 252 and a radio-frequency generator 254. When used, e.g., for an examination of animals said transmitting section can simply be laid on the back of the animal. A metal part 248 which may be provided with surface portions 250 having different shapes, as shown in FIG. 23, will make contact with the skin of the animal. Alternatively the entire transmitting section 246 of the apparatus may replaceably or permanently be accommodated in a plastic envelope, which is not shown here. In that case the transmitting section need not comprise a power supply 252 if power is supplied from the outside, e.g., from the receiving section of the system.

FIG. 24 does not show the ground lead of the transmitting section 246. That ground lead is at the same potential as the ground lead of the receiving section and the shield on the receiving electrode.

Figure 25A:
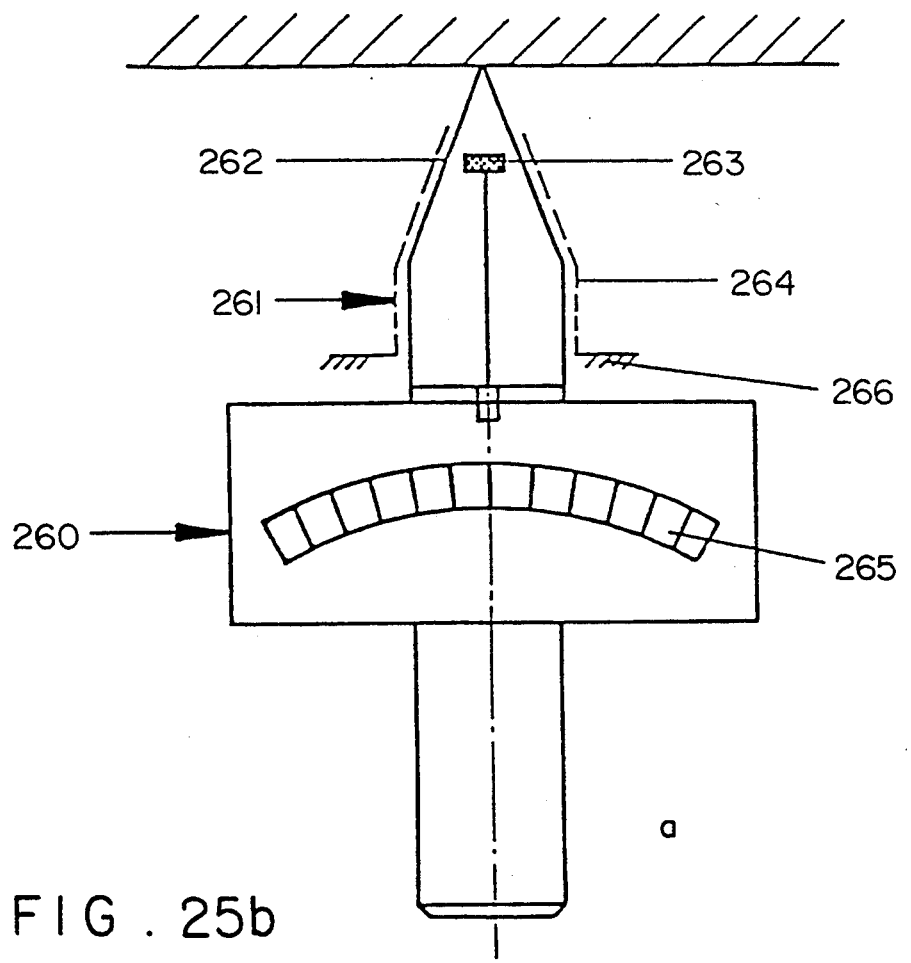
FIGS. 25a and 25b illustrate a receiving section and a sensing body.
Figure 25B:
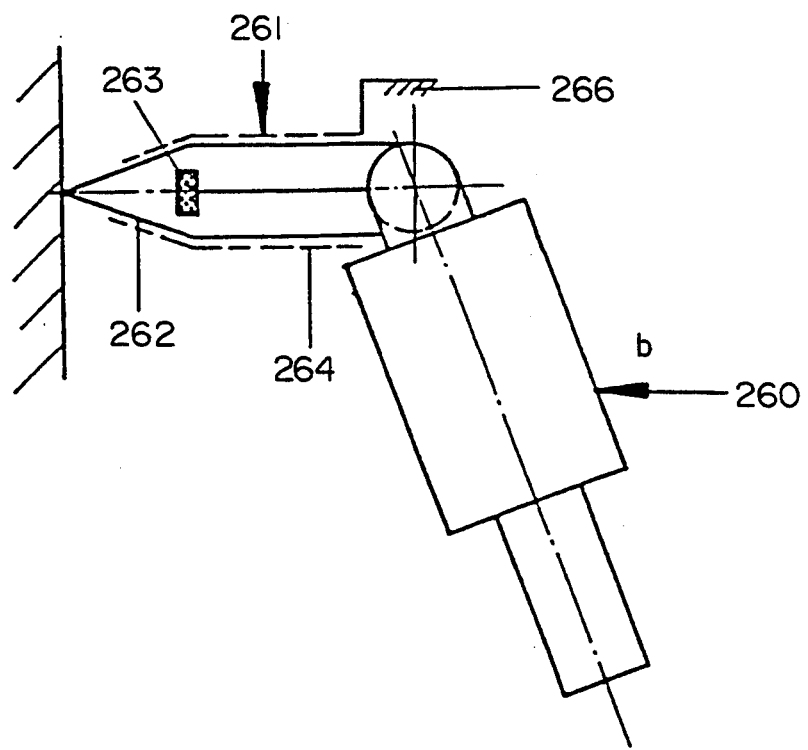

FIG. 25 shows the receiving section 260 of a system as well as the sensing body 261, which is attached to the receiving section and comprises an electrode 263 in a housing 262 that is provided with a shield 264 connected to a ground lead 266. Because that combined apparatus does not require a cable for a connection between the receiving section 260 and the sensing body 262, it may well be used for an examination of limbs, e.g., of horses because there are no obstructing cables. The sensing body 261 may be pivoted so that the analog or digital instrument 265 can be read more easily.

That embodiment may comprise only a receiving section 260, which has a ground lead that is connected to the ground lead of the transmitting section and to the shield associated with the receiving electrode and just as in FIG. 24 that ground lead is not shown. The power supply for that receiving section 260 may be incorporated in said section and may be used to supply power also to the transmitting section of the apparatus. The receiving section 260 may alternatively be supplied with power from an external power supply.

Figure 26A:
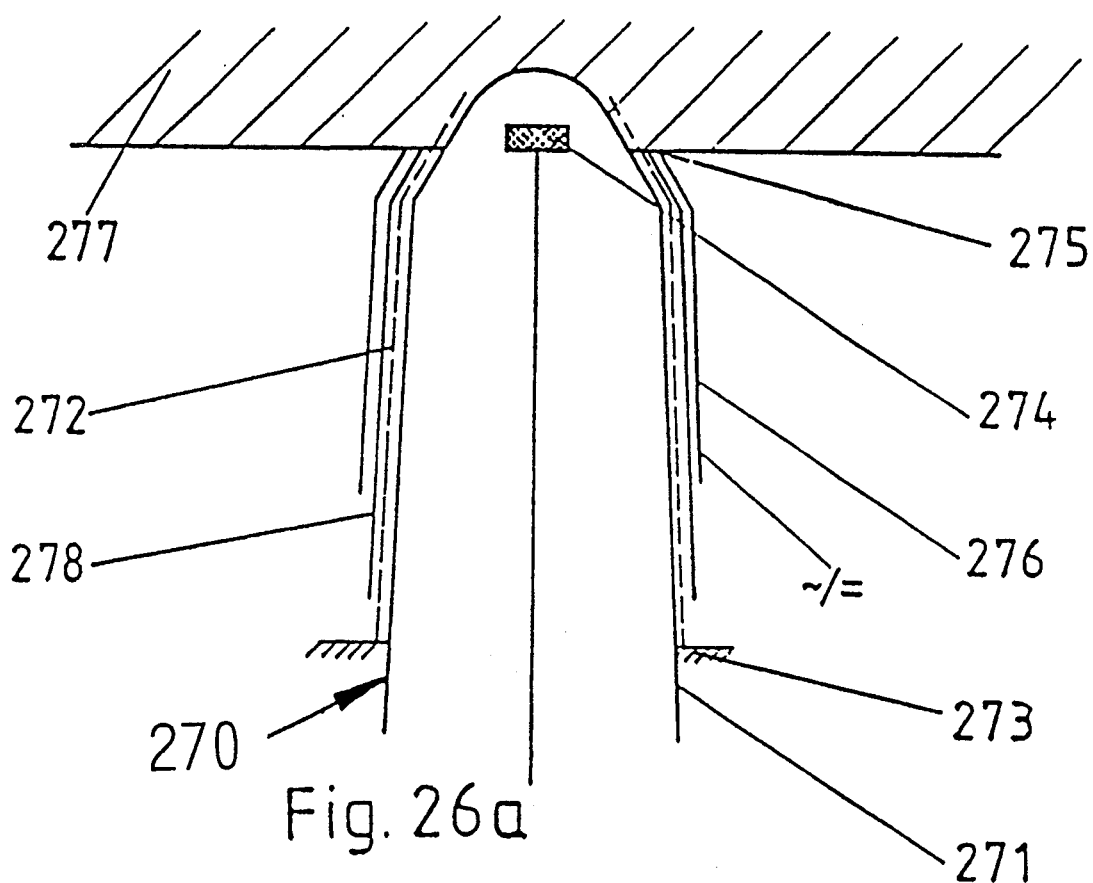
FIGS. 26a and 26b each illustrates a sensing body including an electrode in a housing, which is provided with a shield that is connected to a ground.
Figure 26B:
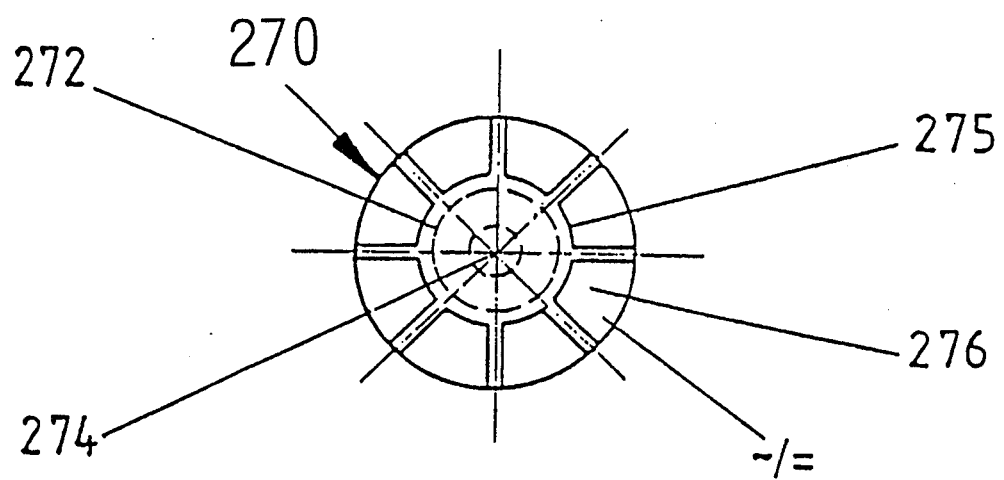

FIG. 26 shows a sensing body 270 comprising an electrode 274 in a housing 271, which is provided with a shield 272 that is connected to ground at 273. Over said shield 272 the sensing body 270 is provided with a circular array of conductive strips 276, which are insulated at 278 from the shield 272. Different potentials in a certain sequence are applied to the conductive strips. Each of the conductive strips 276 has an edge 275, which after the edges of the shield 272 will contact the body 277 to be examined when an adequate pressure is applied to the housing 271. Contact with the conductive strips 276 can be indicated for each of the conductive strips by an indicating device. The sensing body 270 will not be applied in the correct orthogonal position unless the edges 275 of all conductive strips 276 are in contact with the body 277 that is to be examined so that an indication, e.g., a shining of lamps, is given for all conductive strips 276. Any missing indication will indicate the direction of the undesired inclination.

Figure 27:
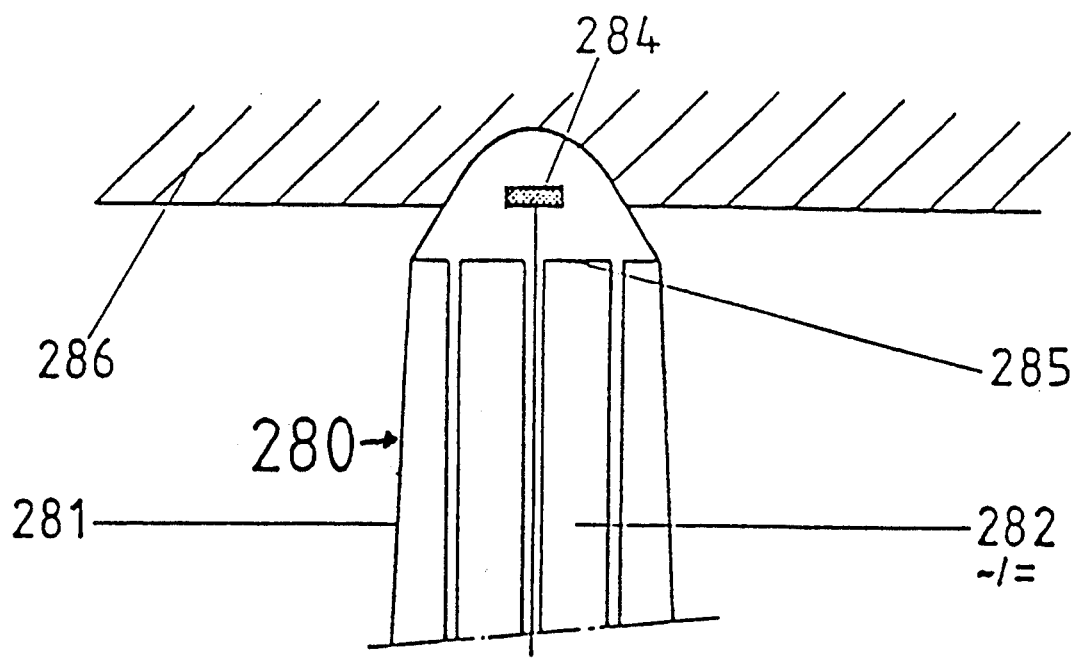
FIGS. 27 and 28 illustrate a sensing body which includes an electrode in a housing.

FIG. 27 shows a sensing body 280 which comprises an electrode 284 in a housing 281. That housing is provided on the outside with a circular array of conductive strips 282, to which low potentials are applied, which preferably differ from each other. Each conductive strip 282 has an edge 285 which will contact the body 286 to be examined when an adequate pressure is applied to the housing 281. In response to that contact the radio-frequency energy is dissipated via the conductive strips 282. That function is the same as that of the conductive edges of the shields described with reference to FIGS. 8, 9, 11, 12, 14, 15, 16 and 26 and also the function that has been described with reference to FIG. 26, i.e., the position in which the sensing body 280 is applied is indicated, i.e., an indication is furnished whether the sensing body is applied in an inclined, incorrect position or at right angles to the surface of the body so that correct measurements can be taken. That embodiment may selectively be operated to perform only one of the functions (shielding and dissipating function) and/or the other of the functions (indication of the position of the sensing body).

Figure 28:
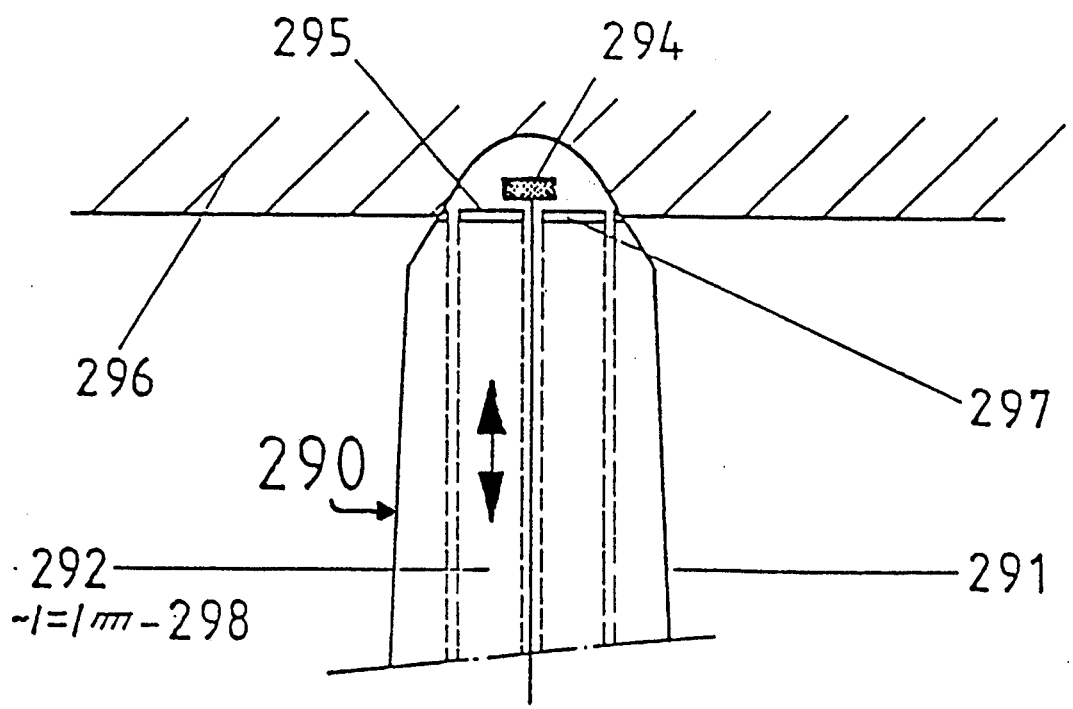

The sensing body 290 shown in FIG. 28 is similar to that shown in FIG. 27 and comprises an electrode 294 which is disposed in a housing 291. Conductive contact strips 292 are provided, which comprise forward portions 297 which protrude forwardly out of the housing 291 to a larger or smaller extent and can be moved to the rear and are connected to ground or to a low potential or suitably to different low potentials. The forward edges of said protruding forward portions 297 of the contact strips 292 will make contact with the surface of the body 296 that is to be examined if an adequate pressure is applied to the sensing body 290 so that the result described with reference to FIG. 27 will also be produced, namely, a shielding function and/or the function of the conductive edges to indicate the position in which the sensing body is applied.

I claim:

1. An apparatus for detecting properties, differences and changes of bodies, comprising:
    an a.c. source having two terminals, a first terminal thereof being adapted to be connected to a body to be examined,
    a sensing electrode disposed in a housing for moving over the surface of the body,
    an electric measuring device coupled between the second terminal of the a.c. source and said sensing electrode,
    wherein said sensing electrode is spaced from a surface of the housing which is moved into contact with the body,
    at least one grounded layer comprising conductive material serving as a shield for the sensing electrode, said shield having a forward edge adapted to contact the body to be examined and to effect a grounding of the a.c. source, wherein a part of the shield protrudes from the housing.

2. An apparatus according to claim 1, further comprising means connected to said electrode for recording measured data, of the body being examined.

3. An apparatus for detecting properties, differences and changes of bodies, comprising:
    an a.c. source having two terminals, a first terminal thereof being adapted to be connected to a body to be examined,
    a sensing electrode disposed in a housing for moving over the surface of the body,
    an electric measuring device coupled between the second terminal of the a.c. source and said sensing electrode,
    wherein said sensing electrode is spaced from a surface of the housing which is moved into contact with the body,
    at least one grounded layer comprising conductive material serving as a shield for the sensing electrode, said shield having a forward edge adapted to contact the body to be examined and to effect a grounding of the a.c. source, and means for varying the position of the shield relative to the electrode.

* * * * *